(12) United States Patent
He

(10) Patent No.: US 12,127,788 B1
(45) Date of Patent: Oct. 29, 2024

(54) BEAUTY INSTRUMENT

(71) Applicant: Hangzhou Ulike Technology Co., Ltd., Hangzhou (CN)

(72) Inventor: Dengshi He, Hangzhou (CN)

(73) Assignee: Hangzhou Ulike Technology Co., Ltd., Hangzhou (CN)

( * ) Notice: Subject to any disclaimer, the term of this patent is extended or adjusted under 35 U.S.C. 154(b) by 0 days.

(21) Appl. No.: 18/527,171

(22) Filed: Dec. 1, 2023

Related U.S. Application Data

(63) Continuation of application No. PCT/CN2023/133373, filed on Nov. 22, 2023.

(30) Foreign Application Priority Data

| Jun. 30, 2023 | (CN) | 202321706159.6 |
| Jun. 30, 2023 | (CN) | 202321711278.0 |
| Jun. 30, 2023 | (CN) | 202321711468.2 |
| Jun. 30, 2023 | (CN) | 202321715889.2 |
| Jun. 30, 2023 | (CN) | 202321716441.2 |
| Jun. 30, 2023 | (CN) | 202321725721.X |

(51) Int. Cl.
*A61B 18/20* (2006.01)
*A61B 18/00* (2006.01)

(52) U.S. Cl.
CPC .. *A61B 18/203* (2013.01); *A61B 2018/00005* (2013.01); *A61B 2018/00476* (2013.01)

(58) Field of Classification Search
CPC ........ A61B 18/203; A61B 2018/00005; A61B 2018/00476
See application file for complete search history.

(56) References Cited

U.S. PATENT DOCUMENTS

2022/0346871 A1   11/2022   Duan

FOREIGN PATENT DOCUMENTS

| CN | 210871255 U | 6/2020 |
| CN | 211093667 U | 7/2020 |
| CN | 212522725 U | 2/2021 |
| CN | 214387634 U | * 10/2021 |
| EP | 3925561 A1 | 12/2021 |
| WO | WO2021003950 A1 | 1/2021 |

* cited by examiner

*Primary Examiner* — Yingchuan Zhang
*Assistant Examiner* — Sebastian X Lukjan
(74) *Attorney, Agent, or Firm* — Nitin Kaushik

(57) ABSTRACT

This application discloses a beauty instrument, including: a housing, where an air inlet hole and an air outlet hole are disposed on the housing; a beauty component, disposed in the housing; and a heat dissipation component, disposed in the housing, and including an airflow generation apparatus and a heat sink, where the heat sink has a first air outlet communicating with the air outlet hole, an air inlet communicating with an air outlet of the airflow generation apparatus, and a second air outlet that is located on a different side wall of the heat sink from the first air outlet, and a size of the second air outlet is less than a size of the first air outlet, where the heat sink absorbs heat, and the second air outlet allows a cooling airflow to flow to a plurality of locations of the heat sink through the air inlet.

20 Claims, 29 Drawing Sheets

BEAUTY INSTRUMENT

CROSS-REFERENCE TO RELATED APPLICATIONS

The present application is a continuation-application of International (PCT) Patent Application No. PCT/CN2023/133373, filed on Nov. 22, 2023, which claims priority of the Chinese patent application No. 202321715889.2, filed on Jun. 30, 2023, the Chinese patent application No. 202321706159.6, filed on Jun. 30, 2023, and the Chinese patent application No. 202321725721.X, filed on Jun. 30, 2023, and the Chinese patent application No. 202321711278.0, filed on Jun. 30, 2023, and the Chinese patent application No. 202321716441.2, filed on Jun. 30, 2023, and the Chinese patent application No. 202321711468.2, filed on Jun. 30, 2023, the entire contents of which are hereby incorporated by reference in their entireties.

TECHNICAL FIELD

This application relates to the field of beauty instruments, and in particular, to a beauty instrument.

BACKGROUND

With the continuous improvement of living standards, beauty instruments gradually enter the daily life of people, and people use the beauty instrument to maintain and repair the skin, so as to enhance external appearances.

In working processes of many beauty instruments, related components inside the beauty instrument generate heat, and heat dissipation needs to be performed for the components that are inside the beauty instrument and that generate heat. As one of beauty instruments, a hair removal instrument can be used to remove skin hair such as underarm hair and leg hair of the human body. The hair removal instrument radiates laser light to hair on the skin. Melanin on the hair absorbs laser energy and converts the laser energy into heat energy that penetrates into hair follicles to destroy the hair follicles and achieve a hair removal effect.

When the hair removal instrument works, much heat is generated inside the hair removal instrument. To discharge the heat in a timely manner, a heat dissipation apparatus is generally mounted inside the hair removal instrument. However, during use, an existing hair removal instrument is still locally overheated or scalded, and a heat dissipation effect thereof is poor.

SUMMARY

A main objective of this application is to provide a beauty instrument, to improve a heat dissipation effect of a hair removal instrument.

To achieve the foregoing objective, this application provides a beauty instrument, including:
a housing, where an air inlet hole and an air outlet hole are disposed on the housing;
a beauty component, disposed in the housing; and
a heat dissipation component, disposed in the housing, and including an airflow generation apparatus and a heat sink, where the heat sink has a first air outlet communicating with the air outlet hole, an air inlet communicating with an air outlet of the airflow generation apparatus, and a second air outlet that is located on a different side wall of the heat sink from the first air outlet, and a size of the second air outlet is less than a size of the first air outlet, where
the heat sink absorbs heat, and the second air outlet allows a cooling airflow generated by the airflow generation apparatus to flow to a plurality of locations of the heat sink through the air inlet.

In the technical solutions provided in this application, during working, the beauty component generates heat, the heat is received by the heat sink, and then the airflow generation apparatus generates a cooling airflow toward the air inlet of the heat sink, to discharge the heat on the heat sink through the air outlet hole on the housing. The heat sink has the first air outlet facing the air outlet hole, and also has the second air outlet disposed on a different side wall from the first air outlet. The size of the second air outlet is less than the size of the first air outlet. The second air outlet is mainly configured to relieve pressure inside the heat sink, to reduce an air pressure difference between an internal air pressure and an external air pressure of the heat sink, so as to increase a possibility that the cooling airflow flows to various locations of the heat sink. Therefore, the second air outlet is disposed, so that the cooling airflow can flow to various locations of the heat sink for heat exchange, thereby effectively alleviating a case in which the housing is locally overheated or scalded, and greatly improving a heat dissipation effect of the beauty instrument.

Figure 1:
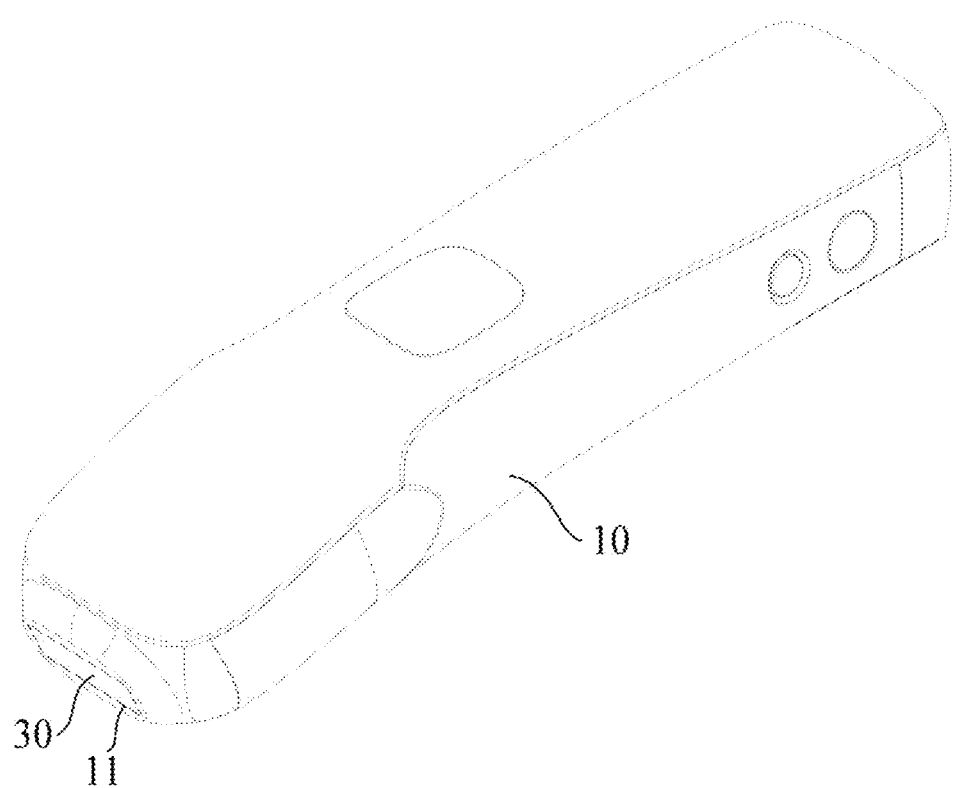
FIG. 1 is a schematic diagram of a structure of a beauty instrument according to an embodiment of this application.

Purpose implementation, functional features, and advantages of this application are further described with reference to the embodiments and the accompanying drawings.

DETAILED DESCRIPTION OF THE EMBODIMENTS

The following clearly and describes the solutions in the embodiments of this application with reference to the accompanying drawings in the embodiments of this application. Clearly, the described embodiments are merely some but not all of the embodiments of this application. All other embodiments obtained by a person of ordinary skill in the art based on embodiments of this application without creative efforts shall fall within the protection scope of this application.

It should be noted that, in the embodiments of this application, all directional indications (such as up, down, left, right, front, and back) are only used to explain a relative location relationship between components in a specific posture (as shown in the accompanying drawings), movement statuses thereof, and the like. If the specific posture changes, the directional indication changes accordingly.

It should also be noted that, when an element is referred to as "being fastened to" or "being disposed on" another element, the element may be directly on the another element or an intermediate element may exist at the same time. When an element is referred to as "being connected to" another element, the element may be directly connected to the another element or an intermediate element may exist at the same time.

In addition, in this application, descriptions such as "first" and "second" are used only for the purpose of description, and should not be understood as an indication or an implication of relative importance or an implicit indication of a quantity of indicated technical features. Therefore, features limited by "first" and "second" may explicitly or implicitly include at least one such feature. In addition, the technical solutions in the embodiments may be combined with each other. However, the combination needs to be based on the fact that a person of ordinary skill in the art can implement the technical solutions. When the combination of the technical solutions is contradictory or cannot be implemented, it should be considered that the combination of the technical solutions does not exist, and does not fall within the protection scope of this application.

An embodiment of this application provides a beauty instrument. Referring to FIG. 1 to FIG. 9, the beauty instrument includes at least a housing 10, a beauty component, and a heat dissipation component. Both the beauty component and the heat dissipation component are disposed in the housing 10. The beauty component is configured to care for a surface of the human skin. During working, the beauty component generates heat in the housing 10, and the heat dissipation component is configured to discharge the heat in the housing 10 to the outside, to prevent the housing 10 from being heated or scalded because the heat is accumulated. The heat dissipation component generally includes an airflow generation apparatus and a heat sink 42. The heat sink 42 is configured to receive the heat in the housing 10, and the airflow generation apparatus is configured to generate a cooling airflow and enable the airflow to flow to the inside of the heat sink 42, so that the heat on the heat sink 42 is taken away by the cooling airflow and discharged through an air outlet hole 12 disposed on the housing 10. It may be understood that the cooling airflow generated by the airflow generation apparatus flows from the outside into the housing 10 through an air inlet hole 13 disposed on the housing 10.

Optionally, the beauty instrument provided in this embodiment of this application may be a laser hair removal instrument, a skin rejuvenation instrument, a whitening instrument, an ultrasonic beauty instrument, or the like, and includes but is not limited thereto. A person skilled in the art may design the beauty instrument based on an actual situation. The hair removal instrument is used as an example below to describe the technical solutions provided in the embodiments of this application. In this case, the beauty component may include a hair removal component 20 and a cold compress component 30. The hair removal component 20 may include a light source. A first light outlet 11 may be disposed on the housing 10. The light source of the hair removal component 20 is configured to emit light toward the first light outlet 11 on the housing 10. The light is received by the cold compress component 30 and emitted to the human skin, to remove hair on the skin. When the light is radiated to the human skin, the human skin receives light energy and converts the light energy into internal energy to generate heat. To improve user experience, the cold compress component 30 may be in contact with the human skin. A surface temperature of the cold compress component 30 is low, and a hot feeling of the human body may be reduced when the cold compress component 30 is in contact with the human body.

It should be noted that the cold compress component 30 includes a semiconductor cooling plate 31 and a lens 32, and the semiconductor cooling plate 31 has a cooling surface and a heating surface. The cooling surface of the semiconductor cooling plate 31 is connected to the lens 32. When the semiconductor cooling plate 31 runs, the cooling surface cools and conducts cold energy to the lens 32, so that a temperature of the lens 32 configured to be in contact with the human skin is low to have a cold compress and soothing effect on the skin, and alleviate a burn caused on the skin by light emitted by the hair removal component 20 or discomfort caused by a high temperature. When the semiconductor cooling plate 31 runs, heat generated by the heating surface is conducted to the heat sink 42 by using a thermally conductive member 60. Optionally, the lens 32 includes a sapphire. That is, the heat sink 42 of the hair removal instrument is mainly configured to dissipate heat for the heating surface of the semiconductor cooling plate 31. It may be understood that light emitted by the hair removal component 20 may be radiated to the human skin after passing through the lens 32, so that when hair removal is performed on a skin region being cared for, cold compress and soothing are performed on the skin region. Alternatively, light emitted by the hair removal component 20 may not pass through the lens 32, but is radiated to the human skin after passing around the lens 32. The lens 32 does not directly perform cold compress on a skin region on which hair removal is being performed, but performs cold compress on the skin around the region. This can also alleviate discomfort caused by a high temperature of the skin.

Optionally, to improve a heat dissipation effect of the hair removal instrument, an air inlet K2, a first air outlet K1, and a second air outlet K3 are disposed on the heat sink 42. The air inlet K2 is connected to an air outlet of the airflow generation apparatus, the first air outlet K1 faces the air outlet hole 12 on the housing 10, the second air outlet K3 is located on a different side wall of the heat sink 42 from the first air outlet K1, and the second air outlet K3 is mainly configured to relieve pressure inside the heat sink 42, to ensure that a cooling airflow can flow to a plurality of locations of the heat sink 42 for heat exchange. During heat dissipation, the cooling airflow generated by the airflow generation apparatus flows to the inside of the heat sink 42 through the air inlet K2; a part of the cooling airflow flows to the outside of the heat sink 42 through the second air outlet K3, and then flows to the outside of the housing 10, and another part of the cooling airflow flows to the outside of the housing 10 through the first air outlet K1 after heat exchange is completed for the cooling airflow inside the heat sink 42. It should be noted that, because the second air outlet K3 is disposed, a difference between an internal air pressure and an external air pressure of the heat sink 42 is reduced. Therefore, after entering the heat sink 42 from the air inlet K2, the cooling airflow can be dispersed to various locations in the heat sink 42 for heat exchange, and then flow out of the heat sink 42 through the first air outlet K1 and the second air outlet K3 respectively. In this way, heat on the heat sink 42 can be evenly dissipated, thereby effectively alleviating a case in which the beauty instrument is locally overheated or scalded.

In addition, the second air outlet K3 is mainly configured to relieve pressure (that is, reduce an air pressure inside the heat sink). Therefore, a diameter of the second air outlet K3 is less than a diameter of the first air outlet K1. After heat exchange inside the heat sink 42, only a small part of the cooling airflow flows out of the heat sink 42 through the second air outlet K3, and then is discharged through the air outlet hole 12 on the housing 10. However, after heat exchange inside the heat sink 42, most of the cooling airflow flows to the outside of the housing 10 through the first air outlet K1. That is, in an embodiment in which the first air outlet K1 directly faces the air outlet hole 12 on the housing 10, after heat exchange is completed for cooling airflow that flows to the inside of the heat sink 42, the cooling airflow is divided into two parts to flow from the inside of the heat sink 42 to the outside thereof. However, after heat exchange inside the heat sink 42, most of the cooling airflow directly flows to the outside of the housing 10 through the air outlet hole 12 on the housing 10. This accelerates discharge of a hot airflow and improves heat dissipation efficiency while alleviating a case in which the housing is locally overheated or scalded.

Optionally, the airflow generation apparatus may include a fan, and the fan generates cooling air to be blown to the heat sink 42, so as to dissipate heat for the heat sink 42.

Optionally, to further improve a heat dissipation effect of the hair removal instrument, the heat sink 42 may further have a third air outlet K4. A function of the third air outlet K4 is the same as a function of the second air outlet K3, and both are configured to relieve pressure inside the heat sink 42, to ensure that the cooling airflow flows more smoothly, evenly, and comprehensively. In some embodiments, the heat sink 42 of the hair removal instrument has both the second air outlet K3 and the third air outlet K4. A diameter of the third air outlet K4 is less than the diameter of the first air outlet K1, and the diameter of the third air outlet K4 may be less than the diameter of the second air outlet K3. During heat dissipation, the cooling airflow generated by the airflow generation apparatus flows to the inside of the heat sink 42 through the air inlet K2; a part of the cooling airflow flows to the outside of the heat sink 42 through the second air outlet K3, and then flows to the outside of the housing 10; another part of the cooling airflow flows to the outside of the heat sink 42 through the third air outlet K4, and then flows to the outside of the housing 10; still another part of the cooling airflow flows to the outside of the housing 10 through the first air outlet K1 after heat exchange is completed for the cooling airflow inside the heat sink 42. That is, after heat exchange is completed for the cooling airflow that flows to the inside of the heat sink 42, the cooling airflow is divided into three parts to flow from the inside of the heat sink 42 to the outside thereof, and finally flow to the outside of the housing 10 through the air outlet hole 12 on the housing 10. When the heat sink has both the second air outlet K3 and the third air outlet K4, the cooling airflow flows more smoothly, evenly, and comprehensively, so that a heat dissipation effect of the heat sink 42 can be significantly improved, and a phenomenon of local heating or scalding is avoided, thereby improving user experience. In some embodiments, the cooling airflow flowing to the outside of the heat sink 42 through the third air outlet K4 may also flow back to the inside of the housing 10, and then flow to the inside of the heat sink 42 under the action of the airflow generation apparatus.

It should be noted that although a part of hot air may flow back to the inside of the housing 10 after the second air outlet K3 and the third air outlet K4 are disposed, experiments have shown that a heat dissipation effect of the heat sink 42 is significantly improved after the second air outlet K3 and the third air outlet K4 are disposed. Compared with a case in which the hot air flows back to the inside of the housing 10 through the second air outlet K3 and the third air outlet K4, thermal impact brought by the hot air may be largely ignored.

Figure 3:
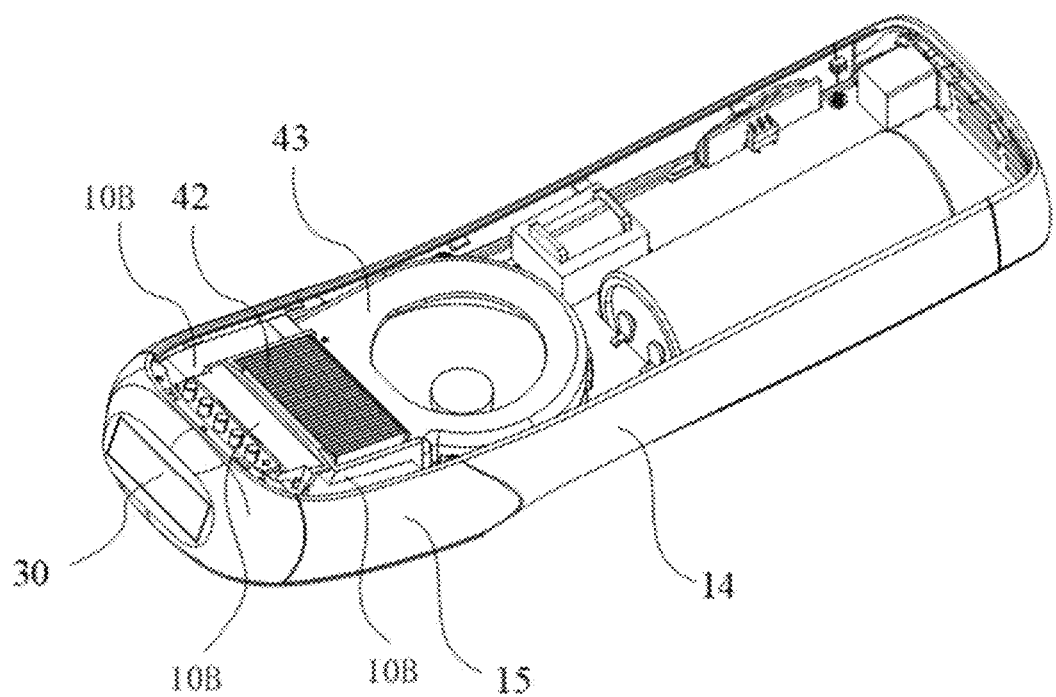
FIG. 3 is a schematic diagram of an internal structure of the beauty instrument in FIG. 2.
Figure 10:
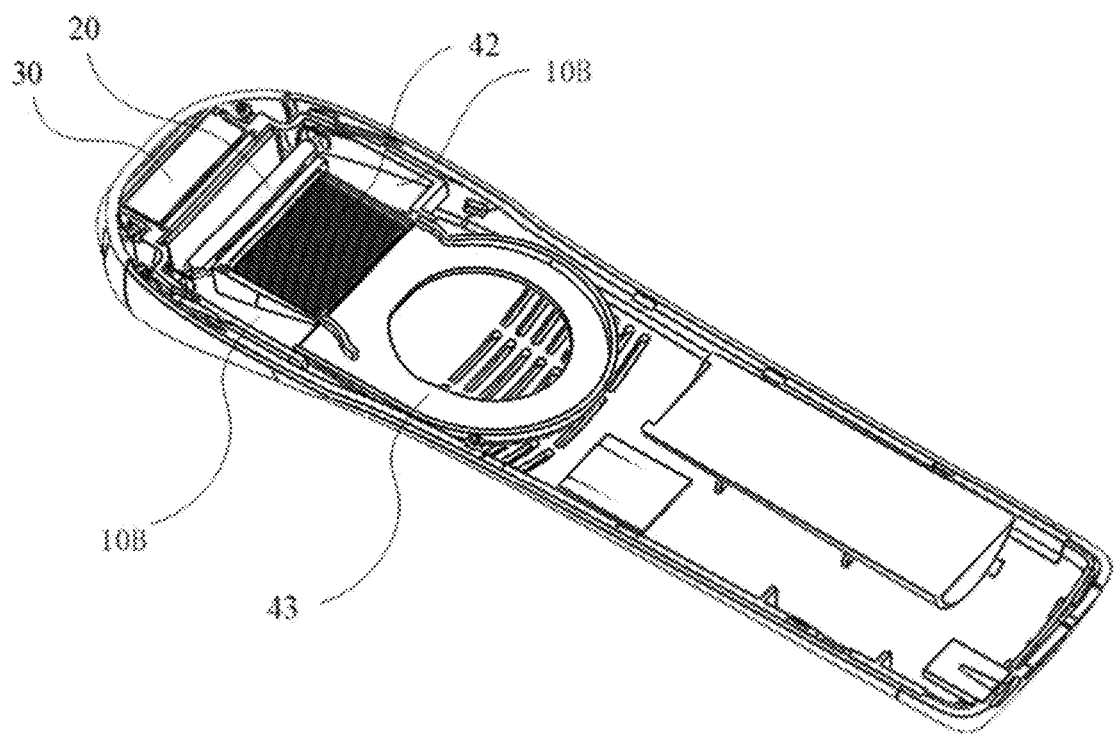
FIG. 10 is a schematic diagram of still another internal structure of the beauty instrument in FIG. 2.

Optionally, referring to FIG. 3 and FIG. 10, the hair removal instrument may include a middle frame 10B, and the middle frame 101B is distributed around a circumference of the heat sink 42 and is substantially U-shaped. One end of the middle frame 10B and the air inlet K2 of the heat sink 42 are jointly connected to the air outlet of the airflow generation apparatus, that is, the cooling airflow generated by the airflow generation apparatus is divided into two parts to separately flow into the heat sink 42 and the middle frame 10B. The other end of the middle frame 10B communicates with the air outlet hole 12 on the housing 10. The hair removal component 20 is disposed in the middle frame 10B to take away, by using the cooling airflow flowing into the middle frame 10B, heat generated by the hair removal component 20 and discharge the heat to the outside of the housing 10 through the air outlet hole 12 on the housing 10. That is, the cooling airflow generated by the airflow generation apparatus is first divided into two parts to separately flow into the heat sink 42 and the middle frame 10B, and the cooling airflow flowing into the heat sink 42 may be further divided into at least two parts based on an actual structural design. For details, refer to the foregoing content. Details are not described herein again. In some embodiments, the cooling airflow generated by the airflow generation apparatus is first divided into two parts to separately flow into the heat sink 42 and the middle frame 10B, and the cooling airflow flowing into the heat sink 42 is further divided into three parts, that is, separately flows to the first air outlet K1, the second air outlet K3, and the third air outlet K4.

Optionally, in addition to the hair removal component 20, the hair removal instrument may further include a skin care component. The skin care component includes a skin care lamp. Light emitted by the skin care lamp is emitted to the human skin by using the cold compress component 30, to implement maintenance on the human skin. When using the hair removal instrument, a user may simultaneously enable a hair removal function and a skin care function of the hair removal instrument, that is, control the skin care component and the hair removal component 20 to simultaneously run, so as to simultaneously remove hair and perform skin care for the human body. Certainly, the hair removal function and the skin care function of the hair removal instrument may be separately used. Enabling of the hair removal function and the skin care function of the hair removal instrument may be controlled separately by using two different buttons, so as to control running and turn-off of the hair removal component 20 and the skin care component.

The foregoing descriptions are mainly descriptions about heat dissipation of the hair removal instrument. A specific structural design of the heat sink 42 provided in this application is described in detail below.

Figure 6:
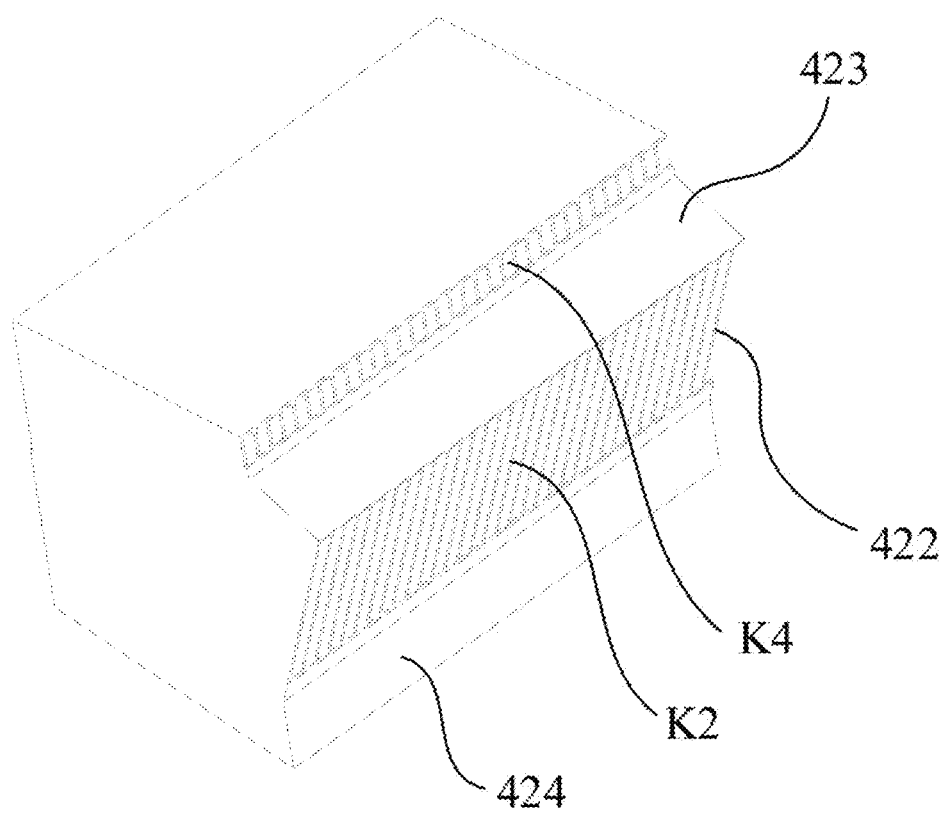
FIG. 6 is a schematic diagram of a structure of a heat sink in FIG. 3.
Figure 7:
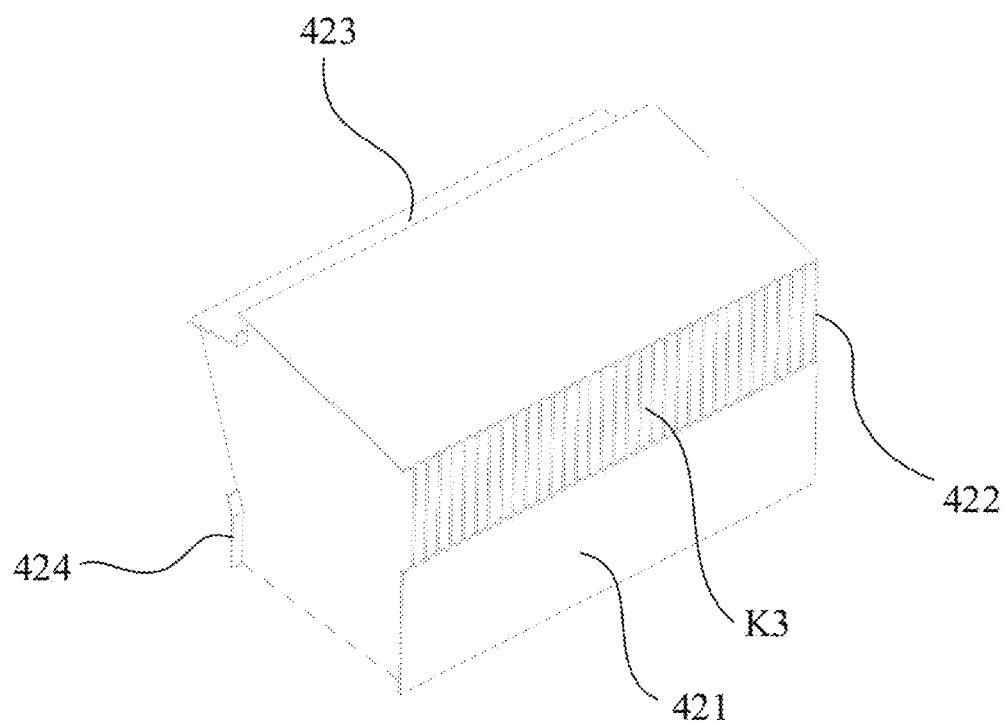
FIG. 7 is a schematic diagram of a structure of the heat sink in FIG. 6 from another perspective.
Figure 8:
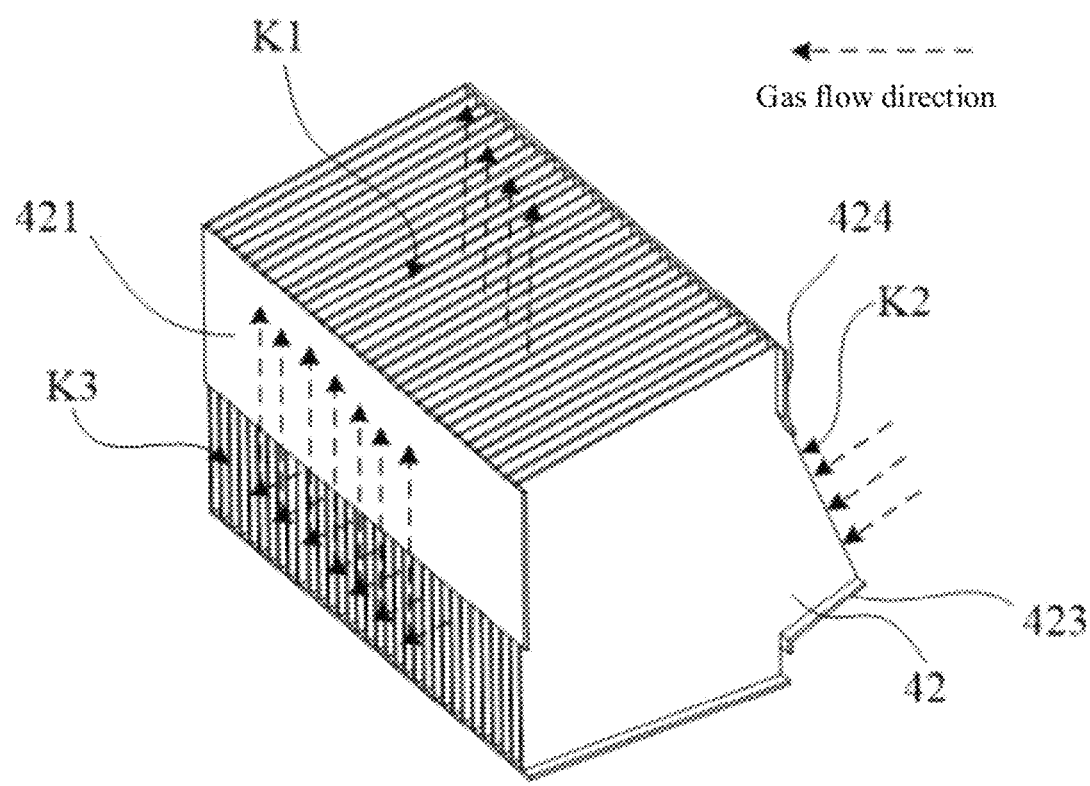
FIG. 8 is a schematic diagram of a structure of the heat sink in FIG. 6 from still another perspective.

In some embodiments, referring to FIG. 6 to FIG. 8, the air inlet K2 and the second air outlet K3 are respectively located on two sides of the first air outlet K1, the heat sink 42 further has a third air outlet K4 that is configured to relieve pressure and that is located on a same side as the air inlet K2, a size of the third air outlet K4 is less than a size of the first air outlet K1, and the third air outlet K4 is staggered from the air inlet K2 and away from the first air outlet K1.

In some embodiments, referring to FIG. 6 to FIG. 9, the heat sink 42 includes several heat dissipation fins 422 disposed at intervals, and several openings facing different directions are formed between two adjacent heat dissipation fins 422. Openings facing the air outlet hole 12 jointly form the first air outlet K1, at least a part of openings facing the beauty component jointly form the second air outlet K3, and openings facing the airflow generation apparatus jointly form the air inlet K2 and the third air outlet K4.

In this embodiment, the heat sink 42 includes several heat dissipation fins 422, and a gap between two adjacent heat dissipation fins 422 is formed as a first channel to allow the cooling airflow to flow in the first channel, so as to perform heat exchange with the heat dissipation fins 422. The first channel has a plurality of openings in different directions, the openings are respectively an opening facing the air outlet hole 12, an opening facing the airflow generation apparatus, and an opening facing the beauty component, and the openings in different directions separately communicate with the first channel. Optionally, the openings facing the air outlet hole 12 are combined to form the first air outlet K1, the openings facing the beauty component are combined to form the second air outlet K3, and the openings facing the airflow generation apparatus are combined to form the air inlet K2 and the third air outlet K4.

In some embodiments, a first stopper 421 is provided at another part of the openings facing the beauty component, and the first stopper 421 is configured to guide a cooling airflow entering from the air inlet K2 to flow toward the first air outlet K1, so that the cooling airflow after heat exchange is discharged from the air outlet hole 12 to the outside.

In this embodiment, a part of the openings that are of the heat sink 42 and that are close to one side of the beauty component are shielded by the first stopper 421, and remaining unshielded opening parts jointly form the second air outlet K3. The internal air pressure of the heat sink 42 is relieved by using the second air outlet K3, so that the cooling airflow can basically flow to various locations of the heat sink 42. A flow direction of a part of the cooling airflow changes after the cooling airflow flows to the first stopper 421, so that the cooling airflow flows to the first air outlet K1, and then flows to the outside of the housing 10 through the air outlet hole 12 on the housing 10.

In some embodiments, the housing 10 includes a handheld part 14 and a care head 15, a connection part between the handheld part 14 and the care head 15 is curved, the beauty component and the heat sink 42 are disposed in the care head 15, the heat sink 42 is located at one end that is of the care head 15 and that is connected to the handheld part 14, the beauty component is located at the other end of the care head 15, and the airflow generation apparatus is disposed at an end that is in the handheld part 14 and that is close to the care head 15.

In this embodiment, the housing 10 includes the handheld part 14 and the care head connected to the handheld part 14, and the connection part between the handheld part 14 and the care head 15 is curved. Therefore, when the user holds the handheld part 14 vertically, a surface that is on the care head 15 and that is used to be in contact with the human skin faces the human body. In this case, the user only needs to slightly tilt the handheld part 14 toward the human body, so that the surface that is on the care head 15 and that is used to be in contact with the human skin can be attached to the human skin to care for the skin. In this way, the beauty instrument better conforms to ergonomics, and is convenient for the user to hold and use. In addition, the beauty instrument can be better attached to the human skin, thereby improving a use effect of the hair removal instrument. Optionally, the beauty component and the heat sink 42 are disposed in the care head 15, and the airflow generation apparatus is disposed at an end that is in the handheld part 14 and that is close to the care head 15.

Figure 9:
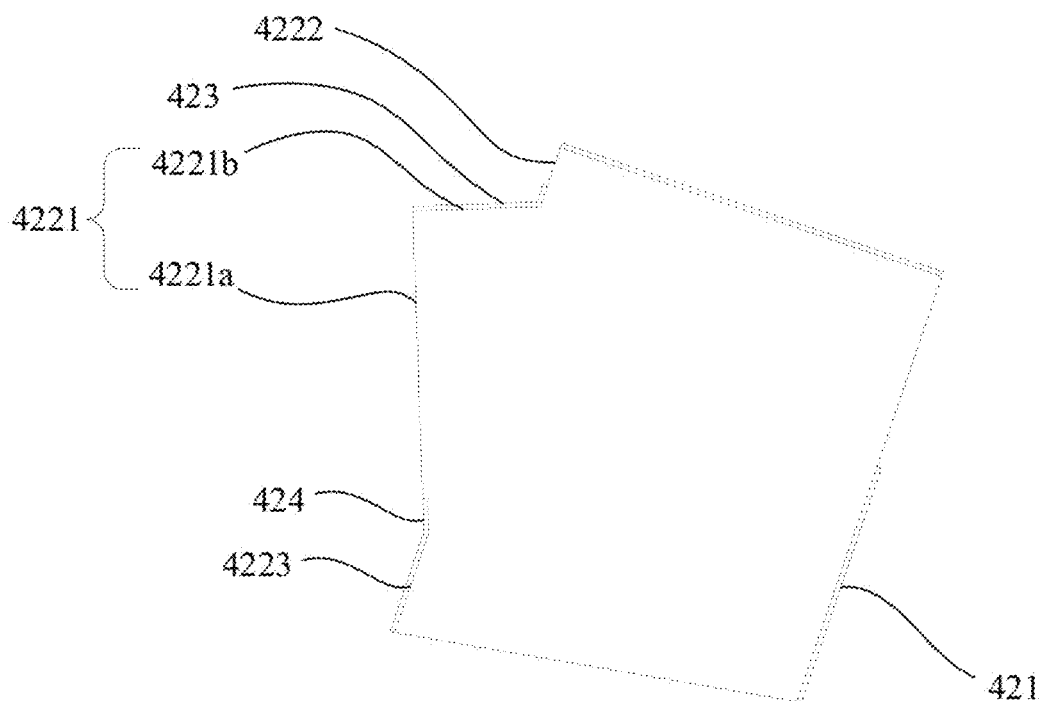
FIG. 9 is an orthographic projection view of the heat sink in FIG. 7.

In some embodiments, referring to FIG. 9, one side of each heat dissipation fin 422 has a protrusion part 4221, each protrusion part 4221 includes a first edge 4221a and a second edge 4221b that intersect with each other, an opening between every two adjacent first edges 4221a forms the air inlet K2 connected to the airflow generation apparatus, and a second stopper 423 is disposed at an opening between every two adjacent second edges 4221b.

In this embodiment, to adapt to bending disposition of the housing 10 to enable the heat sink 42 to be connected to the airflow generation apparatus, one side of each heat sink 422 has the protrusion part 4221, to be connected to the air outlet of the airflow generation apparatus by using the protrusion part 4221. The protrusion part 4221 is located on a side that is of the heat sink 422 and that is close to the airflow generation apparatus, and includes the first edge 4221*a* and the second edge 4221*b*, and the first edge 4221*a* and the second edge 4221*b* form an included angle. The opening between every two adjacent first edges 4221*a* is combined to form the air inlet K2 connected to the airflow generation apparatus, and the second stopper 423 is disposed at the opening between every two adjacent second edges 4221*b*, to avoid the following case: After heat exchange, the cooling airflow is blocked from flowing back into the housing 10 in a direction away from the air outlet hole 12 through the opening between every two adjacent second edges 4221*b*, thereby improving a heat dissipation effect of the hair removal instrument. Optionally, the included angle between the first edge 4221*a* and the second edge 4221*b* is an acute angle.

In some embodiments, referring to FIG. 9, each heat dissipation fin 422 further has a third edge 4222 that is on a same side as the protrusion part 4221 and that intersects with the second edge 4221*b*, and an opening between every two adjacent third edges 4222 forms the third air outlet K4 of the heat sink 42.

In this embodiment, to reduce the difference between the internal air pressure and the external air pressure of the heat sink 42, the opening between every two adjacent third edges 4222 is combined to form the third air outlet K4 of the heat sink 42. The third air outlet K4 and the second air outlet K3 have a same function, and both are configured to relieve pressure of the heat sink 42. Optionally, the third edge 4222 intersects with the second edge 4221*b* and is on a same side as the protrusion part 4221. It should be noted that, a formation region of the third edge 4222 may be adapted to stacking of internal structures of the beauty instrument, so that an internal stacked structure is more compact and stable. In addition, an overall heat dissipation area of the heat sink 42 may be increased. However, when heat dissipation is performed in this region, a high pressure may occur. Therefore, the third air outlet K4 for pressure relief is formed at each of ends of every two adjacent third edges 4222, to further ensure that the cooling airflow flows more smoothly, evenly, and comprehensively.

In some embodiments, referring to FIG. 9, each heat dissipation fin 422 further has a fourth edge 4223 that is on a same side as the protrusion part 4221 and that intersects with the first edge 4221*a*, the fourth edge 4223 extends toward the air outlet hole 12, and a third stopper 424 is disposed at an opening between every two adjacent fourth edges 4223.

In this embodiment, to enable hot air after heat exchange to be discharged as far as possible from the air outlet hole 12, each heat dissipation fin 422 further has the fourth edge 4223 on a same side as the protrusion part 4221, and the fourth edge 4223 extends toward the air outlet hole 12 and is very close to the air outlet hole 12. To prevent the hot airflow from flowing into the housing 10 through the opening between every two adjacent fourth edges 4223, the third stopper 424 is disposed at the opening between every two adjacent fourth edges 4223, to prevent the hot airflow from flowing back.

Figure 5:
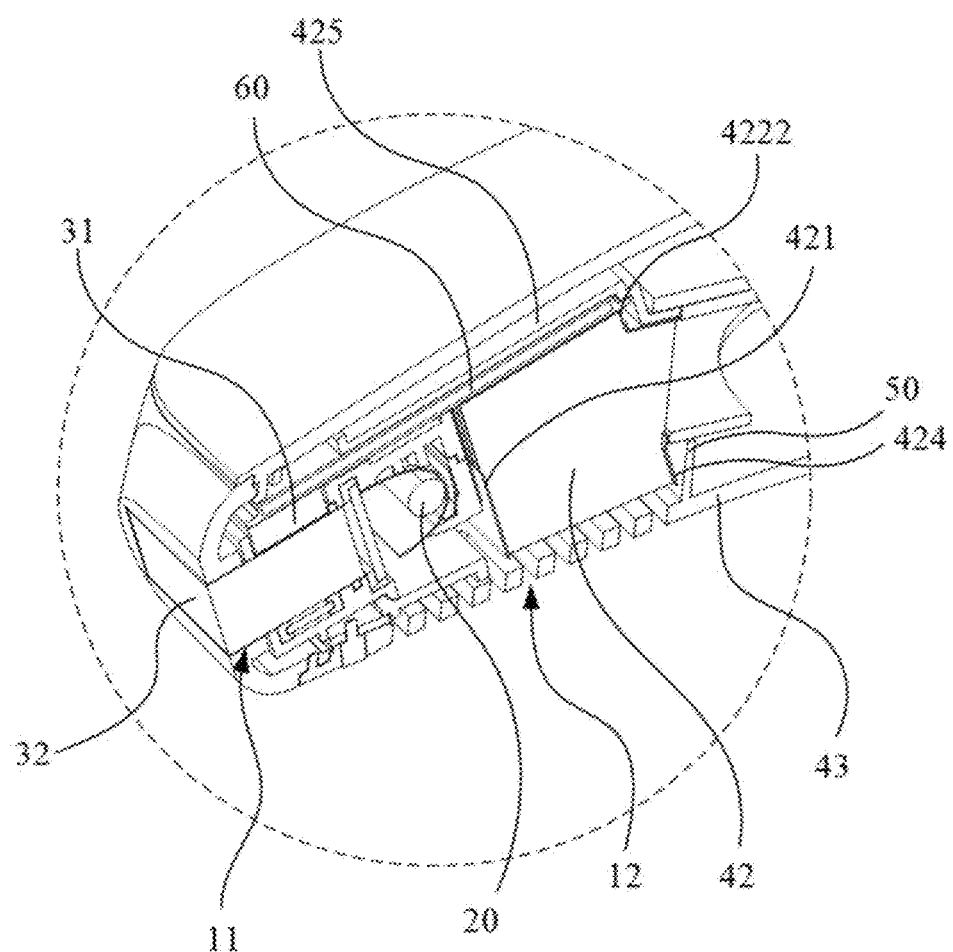
FIG. 5 is a schematic enlarged view at A in FIG. 4.

In some embodiments, referring to FIG. 5, a fourth stopper 425 is disposed on one side of each third edge 4222, the fourth stopper 425 is spaced apart from each third edge 4222, and the fourth stopper 425 is located between the housing 10 and the heat sink 42.

In this embodiment, the fourth stopper 425 is disposed between the housing 10 and the heat sink 42, and the fourth stopper 425 is spaced apart from the third edge 4222 of the heat dissipation fin 422. Space is formed between the fourth stopper 425 and the third edge 4222, so that the hot air flows out through the third air outlet K4. Optionally, an FPC may be disposed on a surface of the fourth stopper 425, and a circuit board may be disposed on a side that is of the fourth stopper 425 and that is close to the airflow generation apparatus, to electrically connect the circuit board to an electrical component located at a bending part of the housing 10 by using the FPC, for example, the hair removal component 20, the cold compress component 30, and the skin care component. The fourth stopper 425 can prevent the hot airflow from being directly blown to the circuit board, thereby reducing a temperature of the circuit board to a specific extent. Optionally, there is an opening between the fourth stopper 425 and the heat sink 42, and the opening communicates with the above-mentioned space.

Optionally, the thermally conductive member 60 is disposed in a shape of a plate, one end thereof extends to the heat sink 42 and covers the top of the heat sink 42, and the other end thereof extends to the cold compress component 30 and is in contact with the heating surface of the semiconductor cooling plate 31. The hair removal component 20 is located between the heat sink 42 and the cold compress component 30. Heat generated by the semiconductor cooling plate 31 is conducted to the heat sink 42 by using the thermally conductive member 60, and then the heat is dissipated to the outside of the housing 10 by using the heat sink 42. Further, the fourth stopper 425 is located between the housing 10 and the thermally conductive member 60. Therefore, the fourth stopper 425 may further have a heat insulation effect, to reduce conduction of heat on the heat sink 42 to the housing 10. Optionally, the thermally conductive member 60 may be a uniform temperature plate.

It should be noted that, in the foregoing embodiments, the first stopper 421, the second stopper 423, the third stopper 424, and the fourth stopper 425 each may be a part of the heat sink 42, a part of the housing 10, or a standalone component. A person skilled in the art may design the stopper based on an actual situation.

Figure 4:
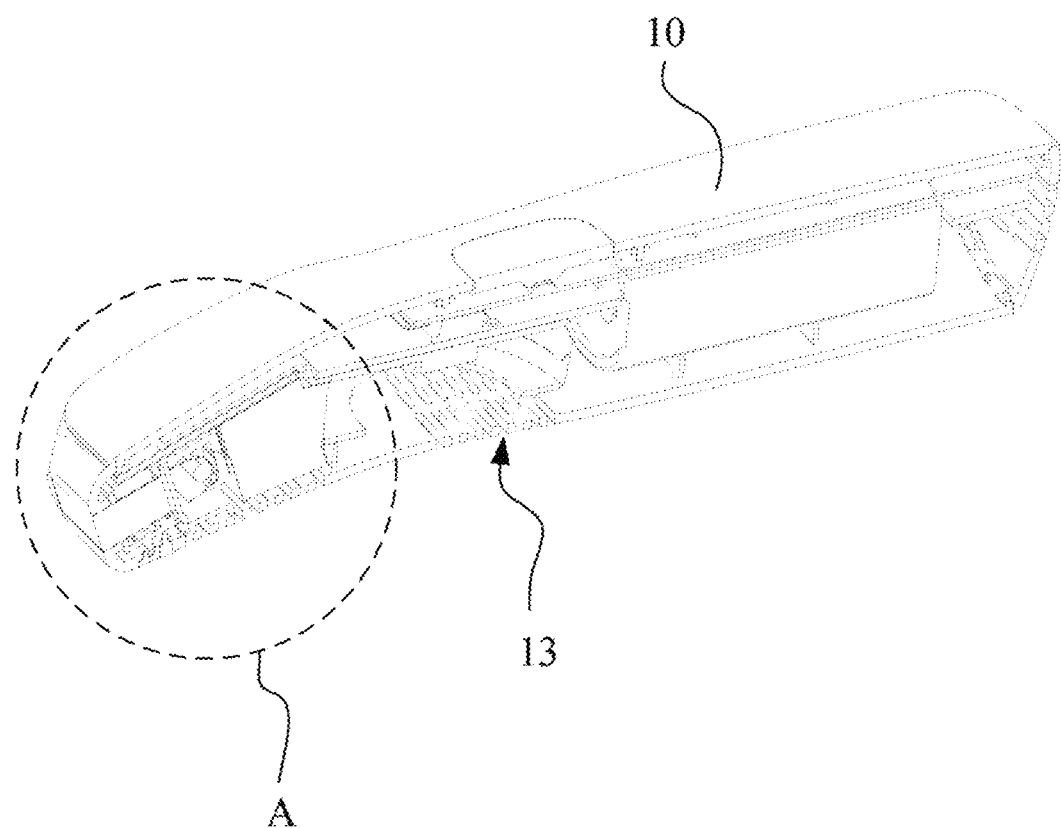
FIG. 4 is a schematic diagram of another internal structure of the beauty instrument in FIG. 2.

In some embodiments, referring to FIG. 4 and FIG. 5, a separation member 50 is disposed between the air inlet hole 13 and the air outlet hole 12 to separate respective space in which the air inlet hole 13 and the air outlet hole 12 are located.

In this embodiment, to further improve a heat dissipation effect, the separation member 50 is disposed between the air inlet hole 13 and the air outlet hole 12 to separate, by using the separation member 50, respective space in which the air inlet hole 13 and the air outlet hole 12 are located. In this way, the hot airflow after heat exchange can be basically discharged to the outside only from the air outlet hole 12, and does not flow back to internal space of the housing 10 in which the air inlet hole 13 is located. Optionally, the separation member 50 includes a convex plate protruding from the inside of the housing 10, one end of the convex plate is connected to an inner wall of the housing 10, the other end thereof abuts on the airflow generation apparatus, and the air inlet hole 13 and the air outlet hole 12 are respectively located on two sides of the convex plate.

Figure 2:
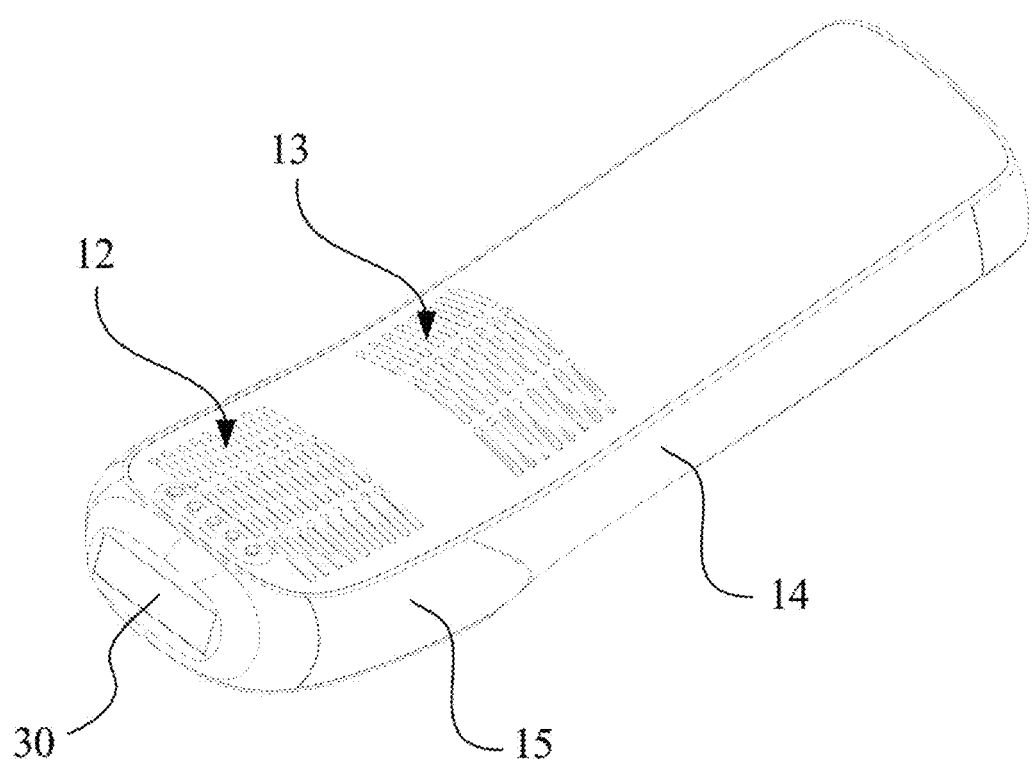
FIG. 2 is a schematic diagram of a structure of the beauty instrument in FIG. 1 from another perspective.

In some embodiments, referring to FIG. 1 to FIG. 3, the air inlet K2 and the second air outlet K3 are respectively located on two sides of the first air outlet K1, and the airflow generation apparatus and the heat sink 42 form an included angle.

In this embodiment, the housing 10 includes a care head 15. The airflow generation apparatus is connected to the heat sink 42 at a location of the care head 15. The air inlet K2 of the heat sink 42 and the first air outlet K1 of the heat sink 42 form an included angle. To adapt to a structural design of the care head 15 and improve a heat dissipation effect of the beauty instrument, the airflow generation apparatus and the heat sink 42 form an included angle. When the airflow generation apparatus and the heat sink 42 form an included angle, each stopper of the heat sink 42 can have a guiding effect on the airflow, to guide most of the airflow to the first air outlet K1 to flow out through the air outlet hole 12 of the housing 10. Compared with a design in which the airflow generation apparatus and the heat sink 42 are on a same horizontal line, an airflow resistance is lower, heat dissipation efficiency is higher, and heat can be dissipated more efficiently and quickly.

An embodiment of this application provides another beauty instrument. Referring to FIG. 1, FIG. 2, and FIG. 8 to FIG. 15, the beauty instrument includes at least a housing 10, a beauty component, and a heat dissipation component. An air inlet hole 13 and an air outlet hole 12 are disposed on the housing 10, and a first gas flow channel 16 and a cavity 18 that communicate with each other are disposed in the housing 10. The beauty component is disposed in the housing 10 and is located in the first gas flow channel 16, the beauty component includes a lamp tube 21 and a reflector 22 disposed around the lamp tube 21, the reflector 22 is open on two opposite sides in a gas flow direction of the first gas flow channel 16 to allow gas to pass through, and a second opening 22a is disposed on the reflector 22 or on one side of the reflector 22. The heat dissipation component is disposed in the housing 10, and the heat dissipation component includes an airflow generation apparatus. An air inlet of the airflow generation apparatus communicates with the air inlet hole 13, an air outlet of the airflow generation apparatus communicates with a gas inlet 16a at one end of the first gas flow channel 16, and a gas outlet 16b at the other end of the first gas flow channel 16 communicates with the air outlet hole 12. A first opening 16c is disposed on one side wall of the first gas flow channel 16, the cavity 18 communicates, by using the first opening 16c and the second opening 22a, with space enclosed by the reflector 22, the cavity 18 is formed with a third opening 18a, and the third opening 18a communicates with the air outlet hole 12.

Figure 11:
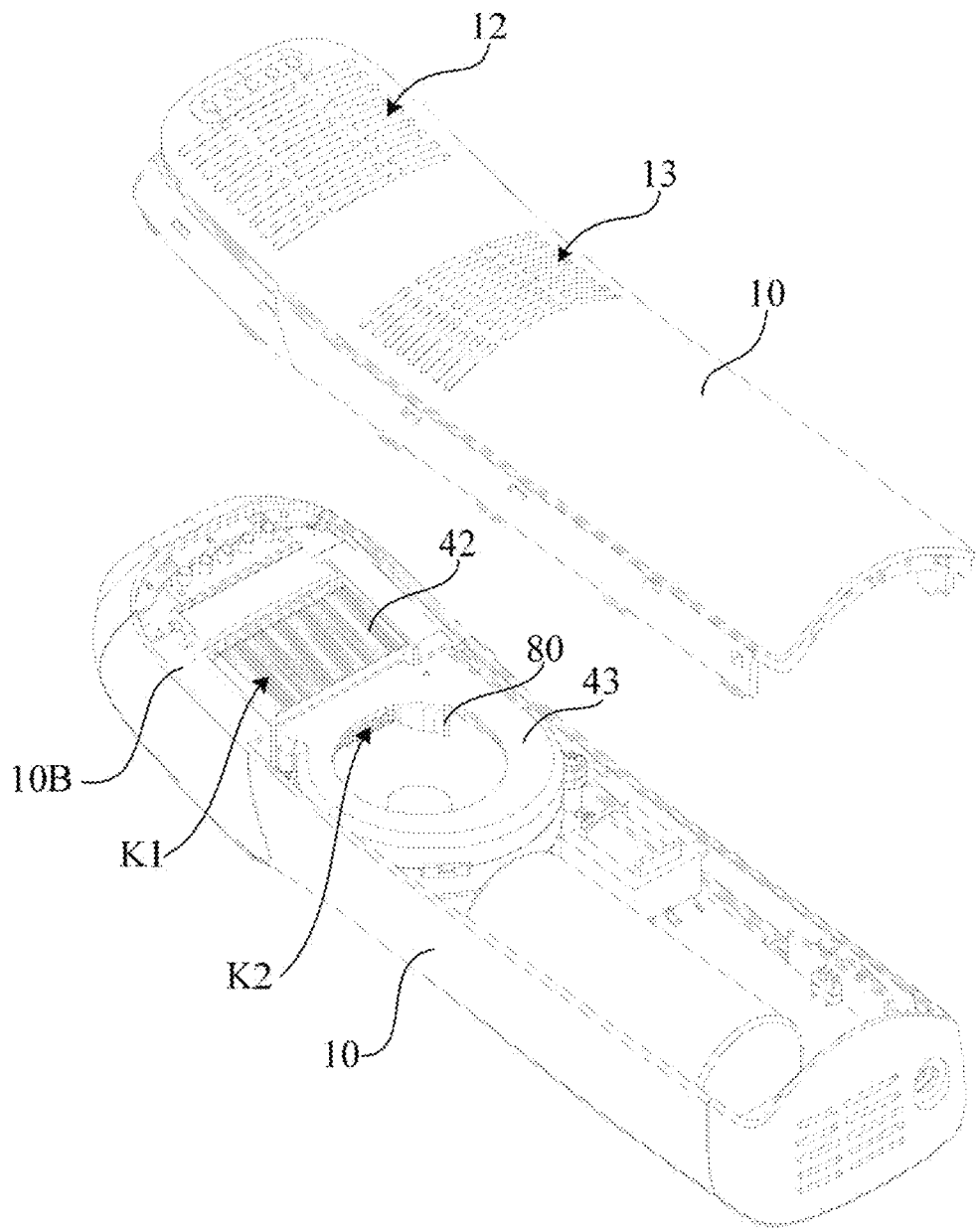
FIG. 11 is an exploded diagram of a beauty instrument according to an embodiment of this application.

In this embodiment, as shown in FIG. 11, the housing 10 is internally hollow and includes an upper housing and a lower cover, and the upper housing and the lower cover enclose an accommodation cavity to accommodate the beauty component and the heat dissipation component. The beauty component is configured to care for a surface of the human skin. During working, the beauty component generates heat in the housing 10, and the heat dissipation component is configured to discharge the heat in the housing 10 to the outside, to prevent the housing 10 from being heated or scalded because the heat is accumulated.

Figure 12:
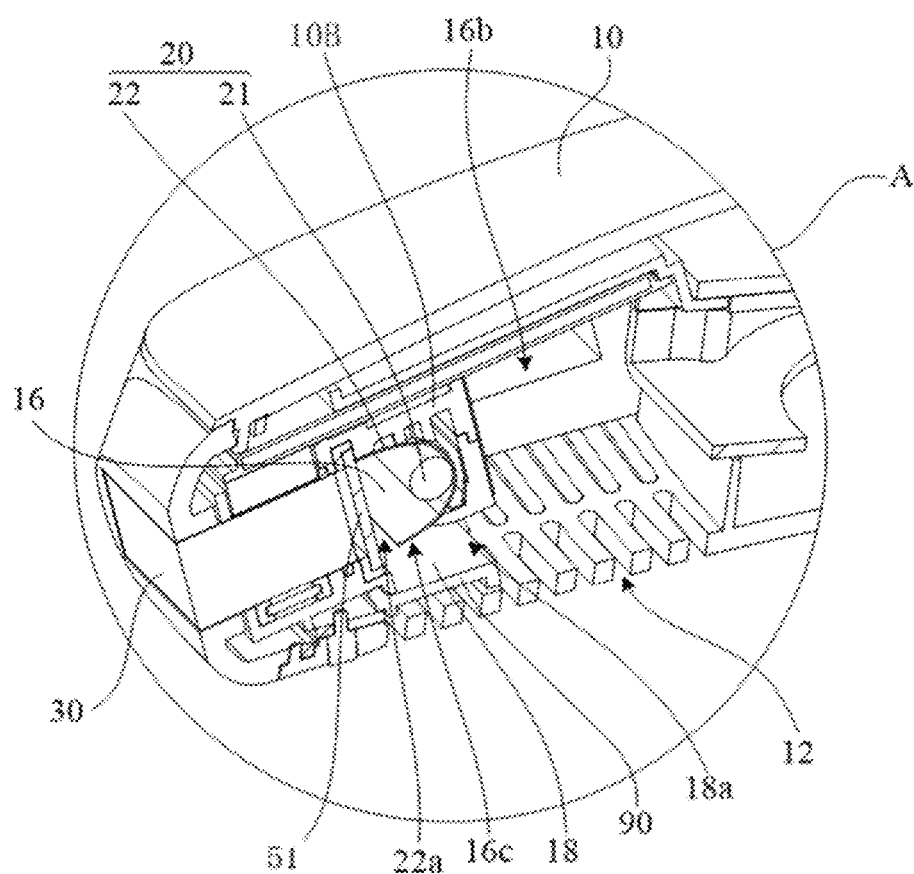
FIG. 12 is another schematic enlarged view at A in FIG. 4.
Figure 14:
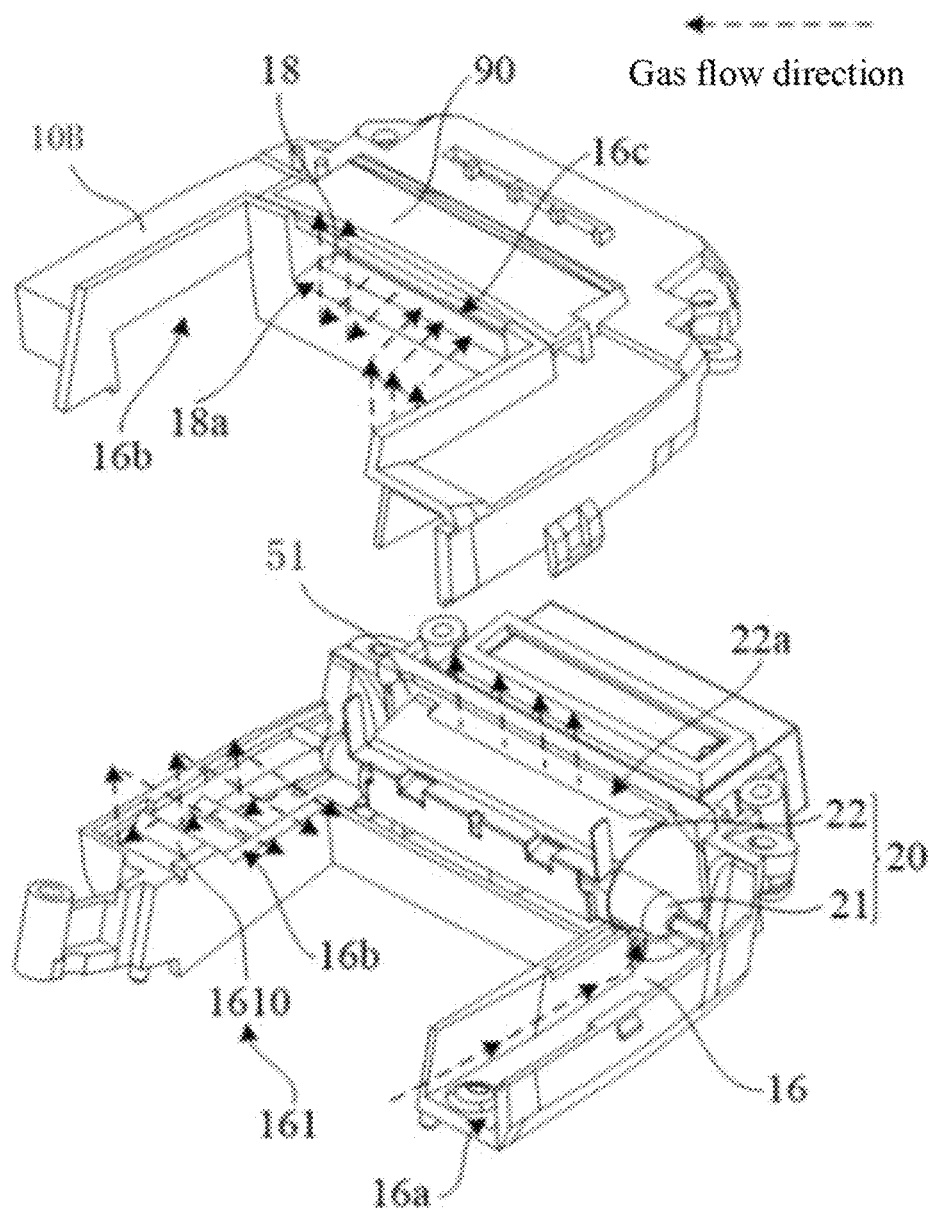
FIG. 14 is an exploded diagram of the middle frame in the embodiment in FIG. 13.

Optionally, the beauty instrument provided in this embodiment of this application may be a laser hair removal instrument, a skin rejuvenation instrument, a whitening instrument, an ultrasonic beauty instrument, or the like, and includes but is not limited thereto. A person skilled in the art may configure the beauty instrument based on an actual situation. Correspondingly, the beauty component includes an electrode component, an LED component, and an ultrasonic component. The hair removal instrument is used as an example below to describe the technical solutions provided in the embodiments of this application. In this case, as shown in FIG. 2, FIG. 12, and FIG. 14, the beauty component may include a hair removal component 20, and a cold compress component 30 may be correspondingly disposed. The hair removal component 20 may include a lamp tube 21 and a reflector 22. The reflector 22 is disposed around the lamp tube 21, and the reflector 22 may be arc-shaped, and surround the lamp tube 21. A first light outlet 11 may be disposed on the housing 10, and the lamp tube 21 of the hair removal component 20 is configured to emit light. Light emitted to the first light outlet 11 is received by the cold compress component 30 and emitted to the human skin, to remove hair on the skin. When the light is radiated to the human skin, the human skin receives light energy and converts the light energy into internal energy to generate heat. To improve user experience, the cold compress component 30 may be in contact with the human skin. A surface temperature of the cold compress component 30 is low, and a hot feeling of the human body may be reduced when the cold compress component 30 is in contact with the human body. Optionally, the housing 10 may be disposed substantially in a shape of a strip, the first light outlet 11 may be located at one end of the housing 10, and the air inlet hole 13 and the air outlet hole 12 may be located on one side of the housing 10.

Figure 13:
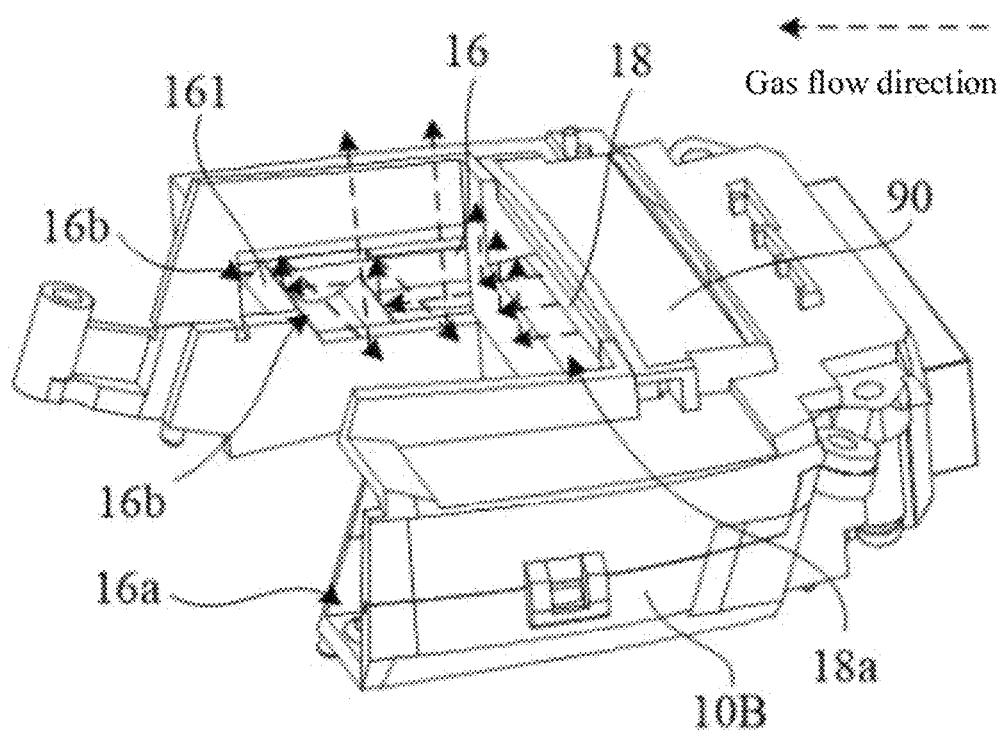
FIG. 13 is a schematic diagram of a structure of a middle frame of the beauty instrument in the embodiment in FIG. 1.

The heat dissipation component includes the airflow generation apparatus, and the airflow generation apparatus generates cooling air to dissipate heat for the beauty component. Optionally, the airflow generation apparatus may include a fan. As shown in FIG. 12 to FIG. 14, the air inlet hole 13 is disposed on the housing 10, so that external gas enters the housing 10. The first gas flow channel 16 is disposed in the housing 10. The beauty component is located in the first gas flow channel 16. Two ends of the first gas flow channel 16 are respectively the gas inlet 16a and the gas outlet 16b. The gas inlet 16a communicates with the airflow generation apparatus, and the gas outlet 16b communicates with the air outlet hole 12 on the housing 10. In addition, the first opening 16c is disposed on one side wall of the first gas flow channel 16, and the cavity 18 is further disposed in the housing 10. The cavity 18 communicates, by using the first opening 16c and the second opening 22a disposed on the reflector 22 or on one side of the reflector 22, with the space enclosed by the reflector 22, that is, communicates with the first gas flow channel 16. The cavity 18 communicates with the air outlet hole 12.

That is, the second opening 22a may be disposed on the reflector 22, or the second opening 22a may not be disposed on the reflector 22, and the second opening 22a is located on one side of the reflector 22, and there is a corresponding interval between the reflector 22 and another structure or component in the housing 10, so that the space enclosed by the reflector 22 communicates with the cavity 18. A shape of the second opening 22a may be a long strip, a wavy line, or the like. This may be set based on an actual situation, and is not limited. It is easy to understand that the cavity 18 substantially communicates with the first gas flow channel 16 by using the first opening 16c in terms of a structure, and the reflector 22 shields the first opening 16c in the first gas flow channel 16, so that the cavity 18 communicates, by using the second opening 22a disposed on the reflector 22 or on one side of the reflector 22, with the space enclosed by the reflector 22. Alternatively, the reflector 22 may be spaced apart from the first opening 16c, and the second opening 22a is correspondingly disposed near the first opening 16c, so that the cavity 18 communicates, by using the first opening 16c and the second opening 22a, with the space enclosed by the reflector 22.

Specifically, during working, the beauty component of the beauty instrument generates heat. The airflow generation apparatus of the heat dissipation component sucks gas at the air inlet of the airflow generation apparatus, and generates cooling air at the air outlet of the beauty component to enable the cooling air to enter the first gas flow channel 16 through the gas inlet 16a of the first gas flow channel 16, so that heat exchange is performed at the beauty component to form hot air. A part of the hot air still flows along the first gas flow channel 16 and flows out from the gas outlet 16b of the first gas flow channel 16 to the air outlet hole 12 to be discharged. Another part of the hot air flows into the cavity 18 from the second opening 22a on the reflector 22 and the first opening 16c of the first gas flow channel 16, flows along the cavity 18, and flows out from the cavity 18 to the air outlet hole 12 to be discharged. The beauty instrument in this application can implement multi-channel gas discharge and heat dissipation for the beauty component, accelerate a heat dissipation speed, and avoid heat accumulation, so as to improve a heat dissipation effect of the beauty instrument, and prevent the beauty instrument from being locally overheated or scalded.

In some embodiments, referring to FIG. 12 and FIG. 14, the beauty component further includes a filter 51. The filter 51 is opposite to the reflector 22, and is configured to filter light emitted by the lamp tube 21. A reflector body edge that is of the reflector 22 and that faces the filter 51 is notched to form the second opening 22a, or an interval between the filter 51 and a reflector body edge that is of the reflector 22 and that faces the filter 51 forms the second opening 22a.

The cold compress component 30 and the beauty component are respectively disposed on both front and rear sides of the filter 51. Considering that the filter 51 includes a layer of filter film, if a temperature of the filter 51 is excessively high, the filter film may be damaged. In this embodiment, the second opening 22a is disposed on a reflector body edge that is of the reflector 22 and that faces the filter 51, or the reflector 22 is spaced apart from the filter 51, and an interval between the reflector 22 and the filter 51 forms the second opening 22a, so that hot air is discharged from the second opening 22a, to help accelerate discharge of an airflow near the filter 51, reduce heat on a side that is of the filter 51 and that faces the beauty component, and prevent the temperature of the filter 51 from being excessively high. In addition, the hot air may be discharged from the second opening 22a, so that heat dissipation efficiency at the filter 51 is improved, thereby reducing heat radiated toward the cold compress component 30, and ensuring a cold compress effect of the beauty instrument.

In some embodiments, referring to FIG. 12 and FIG. 14, the second opening 22a extends toward two opposite sides of the reflector 22. The second opening 22a is in a shape of a long strip, and extends toward two opposite sides of the reflector 22, to maximize a ventilation area of the second opening 22a without leaking light, and increase gas flow that is in the first gas flow channel 16 and that enters the cavity 18 through the second opening 22a, thereby improving a heat dissipation effect.

In some embodiments, referring to FIG. 11 to FIG. 14, the beauty instrument further includes:
 a middle frame 10B, where the middle frame 10B is located in the housing 10, the first gas flow channel 16 is formed on the middle frame 10B, the gas inlet 16a and the gas outlet 16b of the first gas flow channel 16 are respectively located at two opposite ends of the middle frame 10B, and the airflow generation apparatus is opposite to the middle frame 10B and is connected to one end that is of the middle frame 10B and that has the gas inlet 16a.

Specifically, the middle frame 10B is accommodated in the accommodation cavity of the housing 10, and the middle frame 10B may be an independent component, or may be a part of the housing 10, and is integrally formed with the housing 10. In addition, when the middle frame 10B is an independent component, the middle frame 10B may be detachably disposed in the housing 10, and a detachable disposition form may include snap-fit disposition, a screw connection, and the like. The first gas flow channel 16 is formed on the middle frame 10B, and the beauty component is mounted on the middle frame 10B and disposed in the first gas flow channel 16. The middle frame 10B may have a plurality of external structures. For example, the middle frame 10B has a U-shaped structure or an L-shaped structure. This is set based on an actual situation.

In some embodiments, referring to FIG. 12 to FIG. 15, the beauty instrument further includes:
 a baffle 90, where the baffle 90 is located in the housing 10 and is opposite to the middle frame 10B, to form the cavity 18 between the baffle 90 and the middle frame 10B, and the first opening 16c and the third opening 18a are respectively located in directions of two ends of the cavity 18.

Concave space is constructed on the middle frame 10B, and the baffle 90 is opposite to the middle frame 10B, to cover the concave space of the middle frame 10B, so as to form the cavity 18 between the baffle 90 and the middle frame 10B. The baffle 90 may be an independent component, and the baffle 90 is detachably connected to the middle frame 10B. Alternatively, the baffle 90 may be integrally formed with the middle frame 10B. This may be set based on an actual situation. After the gas in the first gas flow channel 16 flows into the cavity 18 through the second opening 22a and the first opening 16c, the gas is blocked by the baffle 90 to flow along the cavity 18, and then flows out from the third opening 18a of the cavity 18 to flow to the air outlet hole 12.

It is easy to understand that the cavity 18 is formed between the baffle 90 and the middle frame 10B, so that a flow direction of gas that is in the first gas flow channel 16 and that flows out through the second opening 22a is correspondingly changed. That is, the gas that is in the first gas flow channel 16 and that flows out through the second opening 22a flows along the cavity 18 and then flows out from the air outlet hole 12, thereby avoiding burning the user because the gas directly flows out from the air outlet hole 12.

Figure 15:
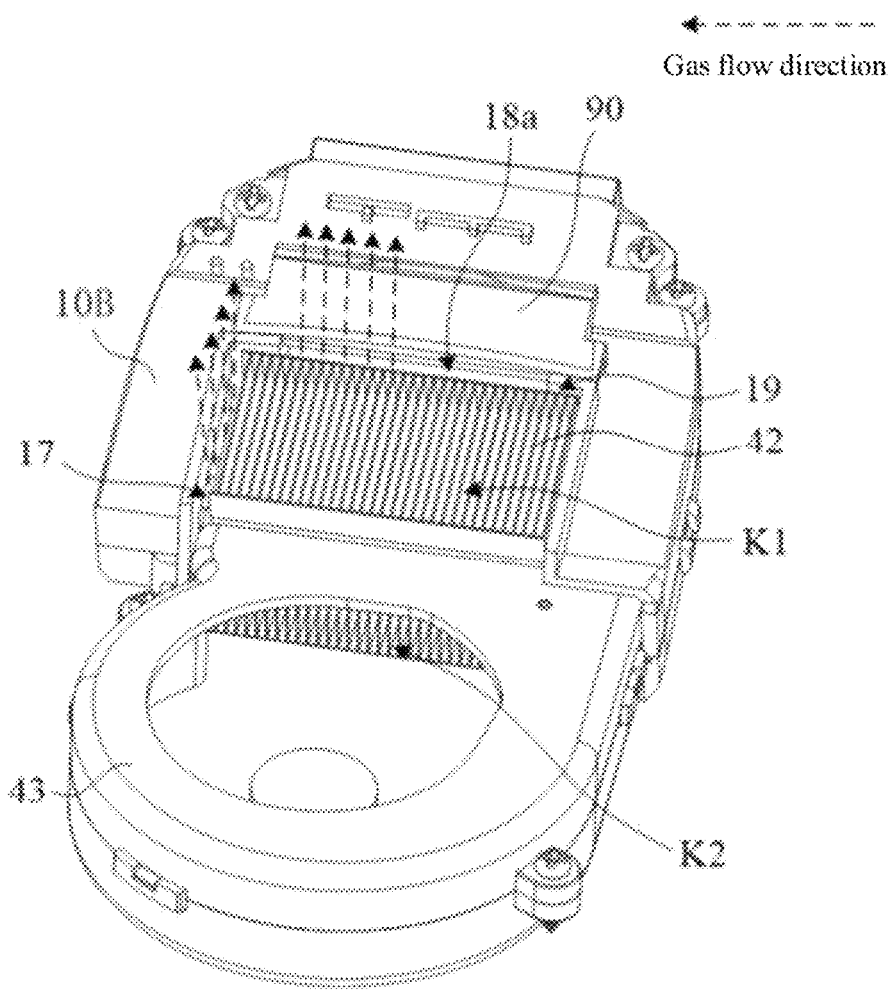
FIG. 15 is a schematic diagram of structures of a middle frame, a heat sink, and a mounting housing of a beauty instrument according to an embodiment of this application.

In some embodiments, referring to FIG. 8, FIG. 11, and FIG. 15, the heat dissipation component further includes a heat sink 42.

The middle frame 10B and the airflow generation apparatus are distributed around a circumference of the heat sink 42, two opposite ends of the middle frame 10B are correspondingly located on two opposite sides of the heat sink 42, and the heat sink 42 has an air inlet K2 connected to the air outlet of the airflow generation apparatus and a first air outlet K1 that faces the air outlet hole 12.

Specifically, the heat sink 42 is configured to dissipate heat for a component inside the beauty instrument. For example, the heat sink 42 is connected to a thermally conductive plate of the cold compress component 30, and heat generated by a heating element of the cold compress component 30 is conducted to the heat sink 42 by using the thermally conductive plate, to dissipate heat. The heat sink 42 has the air inlet K2 and the first air outlet K1. The air inlet K2 is connected to the air outlet of the airflow generation apparatus, to allow cooling air generated by the airflow generation apparatus to flow from the air inlet K2 to the inside of the heat sink 42 for heat exchange. The first air outlet K1 faces the air outlet hole 12 on the housing 10, to allow hot air for which heat exchange is completed to be discharged from the first air outlet K1 to the outside of the housing 10.

In some embodiments, referring to FIG. 13 to FIG. 15, the gas outlet 16b faces the heat sink 42, and the gas outlet 16b and the air outlet hole 12 are respectively located in different side directions of the heat sink 42. An end that is of the middle frame 10B and that is provided with the gas outlet 16b is spaced apart from the heat sink 42 to form a gas passing channel 17, and the gas passing channel 17 is configured to allow gas flowing out of the gas outlet 16b to pass through and flow to the air outlet hole 12.

Specifically, during working, the beauty component generates heat. The airflow generation apparatus of the heat dissipation component absorbs gas from the air inlet hole 13 at the air inlet of the airflow generation apparatus, and generates cooling air at the air outlet of the airflow generation apparatus to enable the cooling air to enter the first gas flow channel 16 through the gas inlet 16a of the first gas flow channel 16, so that heat exchange is performed at the beauty component to form hot air, and the hot air flows out from the gas outlet 16b, passes through the gas passing channel 17 between the middle frame 10B and the heat sink 42, and flows to the air outlet hole 12 to be discharged. This can avoid affecting a heat dissipation effect of the heat sink 42 because the hot air is directly blown to the heat sink 42.

In some embodiments, a part that is of the middle frame 10B and that is located between the gas outlet 16b and the gas inlet 16a is spaced apart from the heat sink 42 to form a gas traveling channel 19, the heat sink 42 further has a second air outlet K3 facing the middle frame 10B, and the second air outlet K3 communicates with the air outlet hole 12 by using the gas traveling channel 19.

Specifically, the heat sink 42 further has the second air outlet K3, the second air outlet K3 faces the middle frame 10B, and the second air outlet K3 has a same function as the first air outlet K1, configured to discharge hot air for which heat exchange is completed in the heat sink 42. Gas discharge and heat dissipation through a plurality of air outlets help increase a heat dissipation speed. Further, the hot air discharged from the second air outlet K3 of the heat sink 42 enters the gas traveling channel 19, and flows along the gas traveling channel 19 to the air outlet hole 12 to be discharged.

In some embodiments, referring to FIG. 8, FIG. 14, and FIG. 15, the third opening 18a faces the heat sink 42, the third opening 18a communicates with the gas traveling channel 19, and is staggered from the second air outlet K3 in a gas traveling direction of the gas traveling channel 19; and two sides of the third opening 18a respectively form an airflow low-pressure side and an airflow high-pressure side, gas flowing out of the second air outlet K3 at least partially flows from the airflow low-pressure side of the third opening 18a into the cavity 18 through the gas traveling channel 19, and the gas in the cavity 18 at least partially flows out of the airflow high-pressure side of the third opening 18a and flows to the air outlet hole 12 through the gas traveling channel 19.

During working, the beauty component generates heat. The airflow generation apparatus of the heat dissipation component absorbs gas at the air inlet of the airflow generation apparatus, and generates cooling air at the air outlet of the airflow generation apparatus to enable the cooling air to enter the first gas flow channel 16 through the gas inlet 16a of the first gas flow channel 16, so that heat exchange is performed at the beauty component to form hot air. A part of the hot air flows into the cavity 18 through the second opening 22a and the first opening 16c, flows out from the third opening 18a of the cavity 18, passes through the gas traveling channel 19 between the middle frame 10B and the heat sink 42, and flows to the air outlet hole 12 to be discharged. This can avoid affecting a heat dissipation effect of the heat sink 42 because the hot air is directly blown to the heat sink 42.

Further, it is easy to understand that, when the gas flowing along the first gas flow channel 16 reaches one side of the beauty component and does not pass through the beauty component, because the gas is low-temperature gas, the airflow low-pressure side is correspondingly formed on one side of the third opening 18a. When the gas passes through the beauty component and reaches the other side of the beauty component, because the gas absorbs heat of the beauty component to form high-temperature gas, the airflow high-pressure side is correspondingly formed on the other side of the third opening 18a.

The second air outlet K3 and the third opening 18a are staggered in the gas traveling direction of the gas traveling channel 19. Further, when gas flowing out of the second air outlet K3 of the heat sink 42 flows along the gas traveling channel 19, the gas passes through the third opening 18a. When the gas flowing out of the second air outlet K3 of the heat sink 42 passes through the third opening 18a, due to impact of an airflow pressure at the location of the third opening 18a, at least a part of the gas correspondingly flows from the airflow low-pressure side of the third opening 18a into the cavity 18, and is mixed with the gas flowing in the cavity 18 through the first opening 16c and the second opening 22a. Another part of the gas may directly flow along the gas traveling channel 19 to the air outlet hole 12 to be discharged.

However, at least a part of the gas in the cavity 18 flows out from the airflow high-pressure side of the third opening 18a, and another part of the gas may flow out from the airflow low-pressure side of the third opening 18a, and both continue to flow to the air outlet hole 12 through the gas traveling channel 19 to be discharged.

In some embodiments, referring to FIG. 11, the heat dissipation component further includes a mounting housing 43, the airflow generation apparatus is disposed in the mounting housing 43, the mounting housing 43 is provided with a shunting member 80 near the air outlet of the airflow generation apparatus, and the shunting member is configured to guide cooling air generated by the airflow generation apparatus into the first gas flow channel 16 and the heat sink 42 respectively.

That is, when the beauty instrument works, the cooling air generated by the airflow generation apparatus of the heat dissipation component is divided by the shunting member 80 into two parts at the air outlet of the airflow generation apparatus. A part of the cooling air enters the first gas flow channel 16 through the gas inlet 16a of the first gas flow channel 16, performs heat exchange at the beauty component to form hot air, and flows out from the gas outlet 16b to the air outlet hole 12 to be discharged. Another pan of the cooling air enters the heat sink 42 through the air inlet K2 of the heat sink 42 to perform heat exchange to form hot air, and flows out from the first air outlet K1 to the air outlet hole 12 to be discharged.

Another embodiment of this application provides a beauty instrument. Referring to FIG. 1, FIG. 2, FIG. 11, and FIG. 13 to FIG. 16, the beauty instrument includes at least a housing 10, a beauty component, and a heat dissipation component. An air inlet hole 13 and an air outlet hole 12 are disposed on the housing 10, and a first gas flow channel 16 is disposed in the housing 10. The beauty component is disposed in the housing 10 and is located in the first gas flow channel 16. The heat dissipation component is disposed in the housing 10, and the heat dissipation component includes an airflow generation apparatus (not shown in the figure). An air inlet of the airflow generation apparatus communicates with the air inlet hole 13, an air outlet of the airflow generation apparatus communicates with a gas inlet 16a at one end of the first gas flow channel 16, and a gas outlet 16b at the other end of the first gas flow channel 16 communicates with the air outlet hole 12. An air guiding structure 161 is disposed in the first gas flow channel 16, and the air guiding structure 161 guides a flow direction of gas in the first gas flow channel 16, so that the gas flows out through a plurality of locations of the gas outlet 16b to the air outlet hole 12.

The flow direction of the gas in the first gas flow channel 16 is different from a discharge direction of the gas outlet 16b. The air guiding structure 161 is disposed in the first gas flow channel 16, and the air guiding structure 161 corresponds to a location of the gas outlet 16b, and is configured to guide, in the first gas flow channel 16, the gas to flow to the gas outlet 16b, so that the gas outlet 16b evenly discharges gas to the air outlet hole 12. Specifically, when the gas reaches an end at which the gas outlet 16b of the first gas flow channel 16 is located, a flow direction thereof is changed under guidance of the air guiding structure 161, so that the gas flows out through the plurality of locations of the gas outlet 16b to the air outlet hole 12. Therefore, the gas in the first gas flow channel 16 evenly flows out, to avoid heat accumulation, thereby improving a heat dissipation effect of the beauty instrument, and preventing the beauty instrument from being locally overheated or scalded.

There may be a plurality of structural forms of the air guiding structure 161.

In some embodiments, as shown in FIG. 13, the air guiding structure 161 is disposed on one inner wall of the first gas flow channel 16 and extends toward the other opposite inner wall of the first gas flow channel 16.

In the flow direction of gas in the first gas flow channel 16, a distance between the air guiding structure 161 and the other opposite inner wall of the first gas flow channel 16 gradually decreases, to step-by-step block the gas flowing at different heights in the first gas flow channel 16, so as to evenly guide the gas to the plurality of locations of the gas outlet 16b.

Specifically, when the gas flows in the first gas flow channel 16 and is to reach an end at which the gas outlet 16b is located, the air guiding structure 161 blocks the gas to change a flow direction thereof. Because the distance between the air guiding structure 161 and the other opposite inner wall of the first gas flow channel 16 gradually decreases, the gas flowing at different locations in the first gas flow channel 16 is blocked by the air guiding structure 161 step by step, so that a flow direction thereof is changed, and the gas is correspondingly guided to different locations of the gas outlet 16b. Optionally, the gas flows in a horizontal direction in the first gas flow channel 16, and gas flowing at different heights is blocked by the air guiding structure 161 to flow in a vertical direction.

Optionally, the air guiding structure 161 may have an entire inclined surface or curved surface that is convexly disposed. This is set based on an actual situation.

Figure 16:
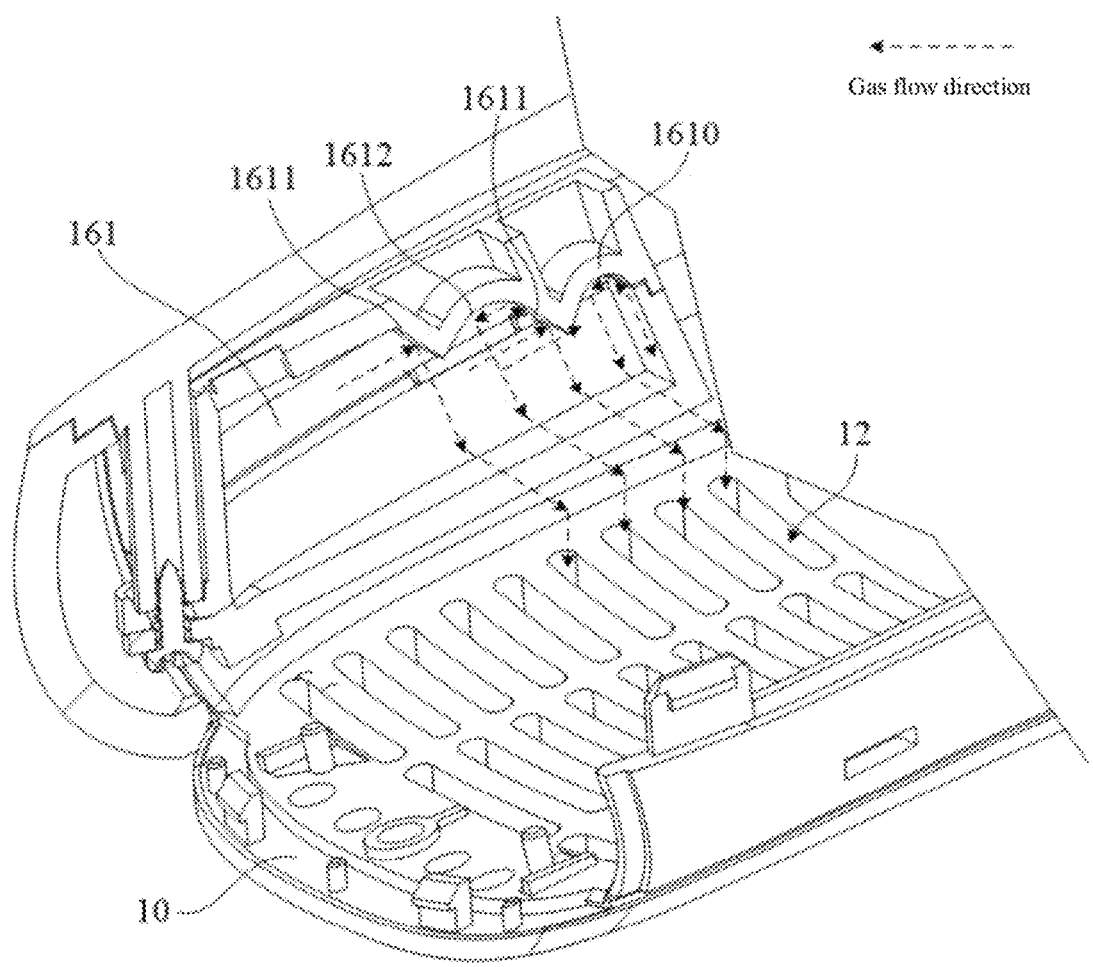
FIG. 16 is a schematic diagram of an internal structure of a beauty instrument according to an embodiment of this application.
Figure 17:
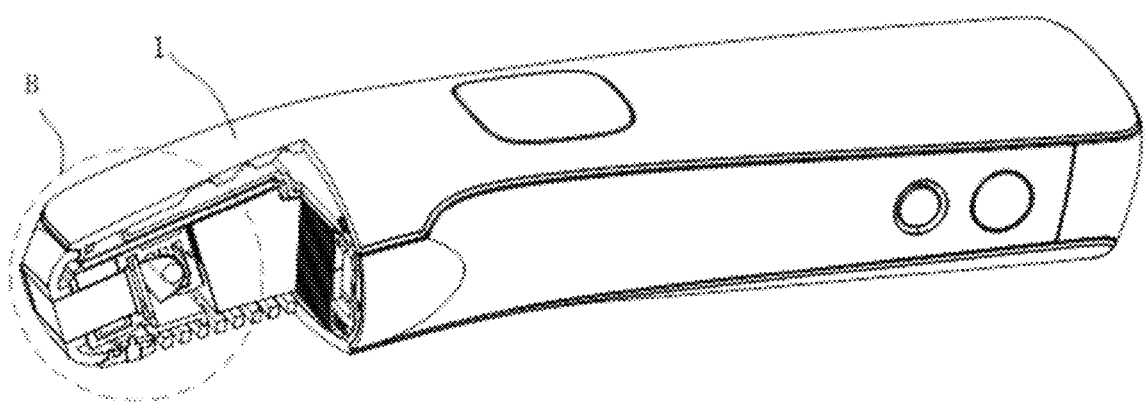
FIG. 17 is a schematic diagram of an internal structure of a beauty instrument according to an embodiment of this application.

In some embodiments, as shown in FIG. 14 and FIG. 16, the air guiding structure 161 includes an air guiding part 1610, the air guiding part 1610 is step-shaped to form a plurality of first air guiding surfaces 1611, and the plurality of first air guiding surfaces 1611 correspondingly block the gas flowing at different heights in the first gas flow channel 16.

Specifically, the air guiding structure 161 is in a structural form of the step-shaped air guiding part 1610, so that the distance between the air guiding structure 161 and the other opposite inner wall of the first gas flow channel 16 gradually decreases in a flow direction of the gas in the first gas flow channel 16 to the air outlet hole 12. When the gas flows in the first gas flow channel 16 and reaches the air guiding part 1610, the gas is blocked by the first air guiding surface 1611 of the air guiding part 1610 to change a flow direction, and is guided to the gas outlet 16b.

The plurality of first air guiding surfaces 1611 are correspondingly a plurality of step surfaces of the step-shaped air guiding part 1610, and the plurality of first air guiding surfaces 1611 on the air guiding part 1610 correspondingly block the gas flowing at different locations in the first gas flow channel 16, to respectively guide the gas at different locations in the first gas flow channel 16 to different locations of the gas outlet 16b.

Optionally, the first air guiding surface 1611 is an inclined surface, a curved surface, or an uneven surface. When the first air guiding plane 1611 is an inclined surface, a slope thereof is set based on an actual situation. When the first air guiding surface 1611 is a curved surface, a curvature thereof is set based on an actual situation. When the first air guiding surface 1611 is an uneven surface, the first air guiding surface 1611 may be a convex or concave surface, for example, a surface formed with a structure such as a saw tooth, a saw blade, or a protrusion. An uneven shape of the first air guiding surface 1611 is set based on an actual situation.

In some embodiments, a second air guiding surface 1612 is further formed on the air guiding part 1610. Any two adjacent first air guiding surfaces 1611 are connected by using the second air guiding surface 1612, and the second air guiding surface 1612 guides a flow direction of gas that flows back due to blocking by the first air guiding surface 1611, so that the gas flows to the gas outlet 16b.

Specifically, when the gas flows in the first gas flow channel 16 and reaches the air guiding part 1610, the gas is blocked by the first air guiding surface 1611 of the air guiding part 1610 to change a flow direction and be dispersed, so that a part of the gas flows back, and another part of the gas flows toward the gas outlet 16b to flow to the gas outlet 16b. The part of gas that flows back due to blocking by the first air guiding surface 1611 may flow along the second air guiding surface 1612, and the second air guiding surface 1612 guides a flow direction of the part of gas, so that the part of gas flows toward the gas outlet 16b to flow to the gas outlet 16b.

In addition, the second air guiding surface 1612 is disposed to guide the flow direction of the gas that flows back, so that the gas flows to the gas outlet 16b, to fill discharge at a vacant location between two discharge locations that are in the gas outlet 16b and that correspond to two adjacent first air guiding surfaces 1611. Therefore, the gas is more evenly discharged from the gas outlet 16b.

That is, because there are a plurality of levels of air guiding surfaces in the gas flow direction, when the gas passes through each air guiding surface, a part of the gas flows out toward the gas outlet 16*b* on the air guiding surface, so that the gas can be prevented from being all accumulated at an end of the first gas flow channel 16, thereby implementing a distributed discharge effect.

Optionally, the second air guiding surface 1612 is a curved surface. A curvature of the second air guiding surface 1612 is set based on an actual situation. In addition, the second air guiding surface 1612 may further be a V-shaped surface, an inclined surface, an uneven surface, or the like.

In some embodiments, the gas outlet 16*b* and the air guiding structure 161 are respectively located on two adjacent or opposite inner walls of the first gas flow channel 16.

During actual disposition, as shown in FIG. 13 and FIG. 14, the gas outlet 16*b* and the air guiding structure 161 are respectively located on two adjacent inner walls of the first gas flow channel 16, and the air guiding structure 161 corresponds to a location of the gas outlet 16*b*. Alternatively, the gas outlet 16*b* and the air guiding structure 161 may be respectively located on two opposite inner walls of the first gas flow channel 16, and the air guiding structure 161 is opposite to a location of the gas outlet 16*b*.

In some embodiments, the beauty instrument further includes:
a middle frame 10B, where the middle frame 10B is located in the housing 10, the first gas flow channel 16 is formed on the middle frame 10B, the gas inlet 16*a* and the gas outlet 16*b* of the first gas flow channel 16 are respectively located at two opposite ends of the middle frame 10B, and the airflow generation apparatus is opposite to the middle frame 10B and is connected to one end that is of the middle frame JOB and that has the gas inlet 16*a*.

In some embodiments, as shown in FIG. 11 and FIG. 15, the heat dissipation component further includes a heat sink 42.

The middle frame 10B and the airflow generation apparatus are distributed around a circumference of the heat sink 42, two opposite ends of the middle frame 10B are correspondingly located on two opposite sides of the heat sink 42, and the heat sink 42 has an air inlet K2 connected to the air outlet of the airflow generation apparatus and a first air outlet K1 that faces the air outlet hole 12.

Optionally, the middle frame 10B is U-shaped to form accommodation space outside the middle frame 10B. The heat sink 42 is located in the accommodation space outside the middle frame 10B. The middle frame 10B and the airflow generation apparatus are disposed around a circumference of the heat sink 42, so that a structure is compact and occupies small internal space of the housing 10.

In some embodiments, referring to FIG. 15, the gas outlet 16*b* faces the heat sink 42, and the gas outlet 16*b* and the air outlet hole 12 are respectively located in different side directions of the heat sink 42. An end that is of the middle frame 10B and that has the gas outlet 16*b* is spaced apart from the heat sink 42 to form a gas passing channel 17, and the gas passing channel 17 is configured to allow gas flowing out of the gas outlet 16*b* to pass through and flow to the air outlet hole 12.

Referring to FIG. 1 and FIG. 17 to FIG. 21, still another embodiment of this application provides a beauty instrument, including:
a housing 10;
a light source 2, disposed in the housing 10;
a cold compress component 30, disposed on a side of the light source 2 in a light exit direction, and configured to export light to the human skin, to care for the skin;
a first optical element 4, disposed between the light source 2 and the cold compress component 30;
a second optical element 5, disposed between the first optical element 4 and the cold compress component 30; and
a first sealing member 6, disposed between the first optical element 4 and the second optical element 5, and configured to seal a gap between the first optical element 4 and the second optical element 5.

The beauty instrument provided in this embodiment of this application may be a hair removal instrument, a skin rejuvenation instrument, a whitening instrument, or the like. The hair removal instrument is used as an example below to describe the technical solutions provided in the embodiments of this application. Specifically, the first optical element 4 and the second optical element 5 in this embodiment have good light transmittance and heat resistance, and may be quartz or glass. Optionally, one of the first optical element 4 and the second optical element 5 is a filter 51, the filter 51 is configured to filter light, the other of the first optical element 4 and the second optical element 5 is a heat insulation piece 41, and the heat insulation piece 41 is configured to block heat radiated by the light source 2 to the cold compress component 30. In this embodiment, the first optical element 4 is the heat insulation piece 41, and the second optical element 5 is the filter 51. In this embodiment, the housing 10 has a mounting structure inside, configured to mount the light source 2, the cold compress component 30, the filter 51, and the heat insulation piece 41. The housing 10 may include an upper cover and a lower housing, and the upper cover and the lower housing enclose the mounting structure, so that the light source 2, the filter 51, the heat insulation piece 41, and the cold compress component 30 are mounted in the mounting structure. The housing 10 has an open end, and the cold compress component 30 is disposed at the open end of the housing 10, and is configured to be in contact with the human skin to perform cold compress on the skin, so as to reduce a skin temperature. The light source 2 in this embodiment is configured to provide intense pulse light or laser light to care for the skin. Optionally, the light source 2 may be a lamp tube 21. A reflector 22 is disposed on one side of the lamp tube 21. The reflector 22 partially surrounds the lamp tube 21 and has an opening facing the cold compress component 30. The lamp tube 21 is disposed in a width direction of the housing, and the lamp tube 21 may be a laser lamp, a xenon lamp, an LED lamp, or the like.

In this embodiment, the heat insulation piece 41 is disposed between the light source 2 and the cold compress component 30, and the filter 51 is disposed between the heat insulation piece 41 and the cold compress component 30. The filter 51 is configured to filter light that passes through the filter. Specifically, the light emitted by the light source 2 may be intense pulse light. In this case, the intense pulse light is polychromatic light, and includes light with different wavelengths, including ultraviolet light whose wavelength is below 400 nm. The ultraviolet light is harmful to the human skin and eyes. However, the filter 51 in this embodiment can filter out harmful light with this wavelength, and retain light with a wavelength applicable to hair removal and beauty treatment. The filter 51 has good light transmittance and heat resistance. Optionally, the filter 51 is quartz. The heat insulation piece 41 may block heat radiated by the light source 2, to reduce heat radiated to the cold compress component 30. In addition, because the heat insulation piece 41 is disposed between the light source 2 and the filter 51, the heat insulation piece 41 may further protect the filter 51, to reduce a risk that a filter layer on the filter 51 falls off or is damaged because a temperature of the filter 51 is excessively high. The heat insulation piece 41 may be a transparent low-thermally-conductive material such as glass. The cold compress component 30 in this embodiment is configured to guide intense pulse light to the human skin, and the intense pulse light acts on hair follicles of the skin, so that structures of the hair follicles change, thereby achieving a hair removal effect. During hair removal, the cold compress component 30 is in contact with the human skin and performs cold compress on the skin to reduce a burning feeling generated on the skin during hair removal. Further, the heat insulation piece 41 is disposed between the cold compress component 30 and the light source 2, to block heat radiated by the light source 2. This greatly reduces heat radiated to the cold compress component 30, and improves a cold compress effect of the cold compress component on the skin, thereby reducing a burning feeling generated during hair removal, and improving user experience. In some embodiments, the cold compress component 30 includes a lens 32 configured to be in contact with the human skin and a semiconductor cooling plate 31, and a cooling surface of the semiconductor cooling plate 31 is in contact with the lens 32 to reduce a temperature of the lens 32. The lens 32 may be a sapphire. During hair removal, the sapphire is in contact with the skin, thereby reducing a surface temperature of the human skin and further reducing a burning feeling of the skin.

Figure 18:
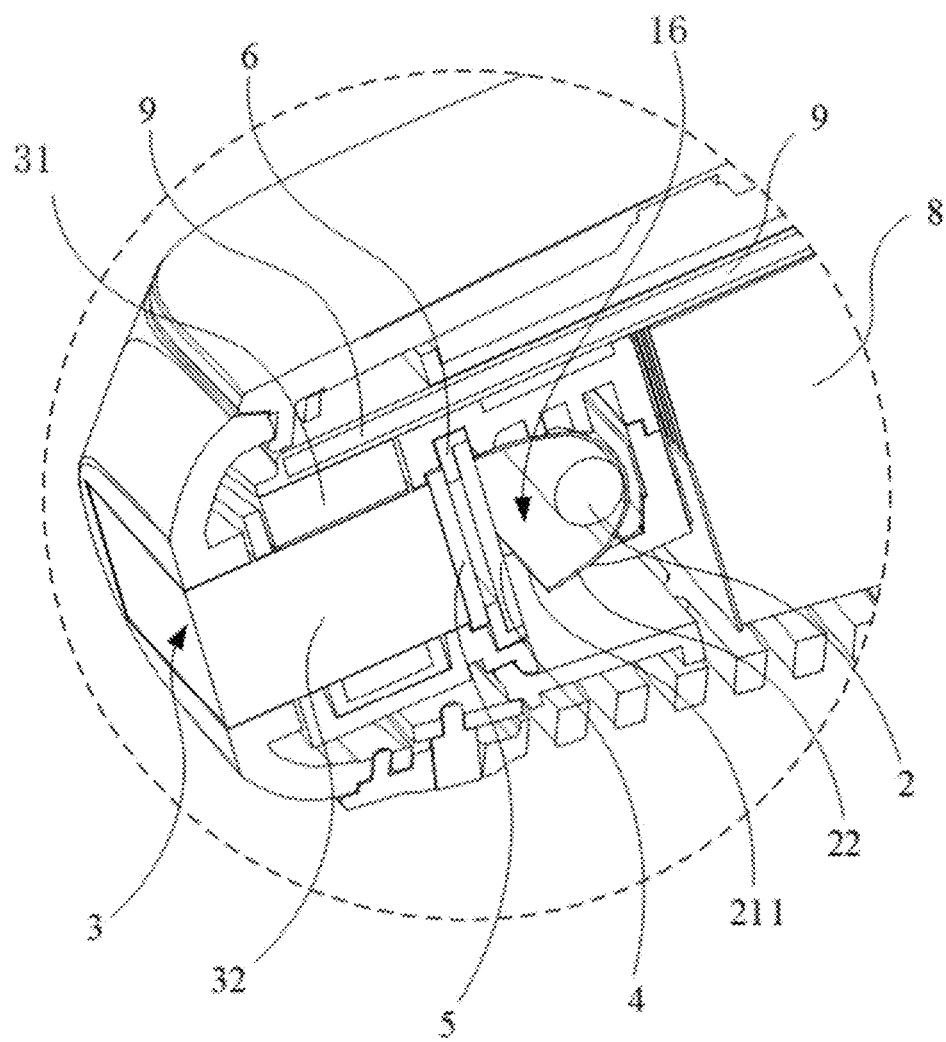
FIG. 18 is a schematic enlarged view at B in FIG. 17.

When the cold compress component 30 works, a temperature of the lens 32 of the cold compress component 30 is low, and a temperature around the light source 2 inside the housing 10 is high. As a result, fog easily occurs on an end face that is of the lens 32 and that is close to the light source. In this case, referring to FIG. 17 to FIG. 21, the first sealing member 6 is disposed between the first optical element 4 and the second optical element 5, to seal the gap between the first optical element 4 and the second optical element 5. Further, the second optical element 5 is attached to the cold compress component 30, as shown in FIG. 18.

Specifically, the first optical element 4 is the heat insulation piece 41, and the second optical element 5 is the filter 51. The heat insulation piece 41 separates the inside of the housing 10 into first space used to mount the light source 2 and second space used to mount the cold compress component 30, to block heat out of the second space. In this embodiment, the second space is sealed by using the first sealing member 6, to avoid a phenomenon that fog occurs because hot air enters the second space and is in contact with the lens 32 with a low temperature. Specifically, the first sealing member 6 seals the gap between the heat insulation piece 41 and the filter 51, to prevent external hot air from entering. In addition, the filter 51 is attached to the lens 32, to block an external cold airflow generated by the cold compress component 30, thereby avoiding a phenomenon that fog occurs in the lens 32 and an optical element in the gap, and improving a service life and performance of the hair removal instrument.

Figure 19:
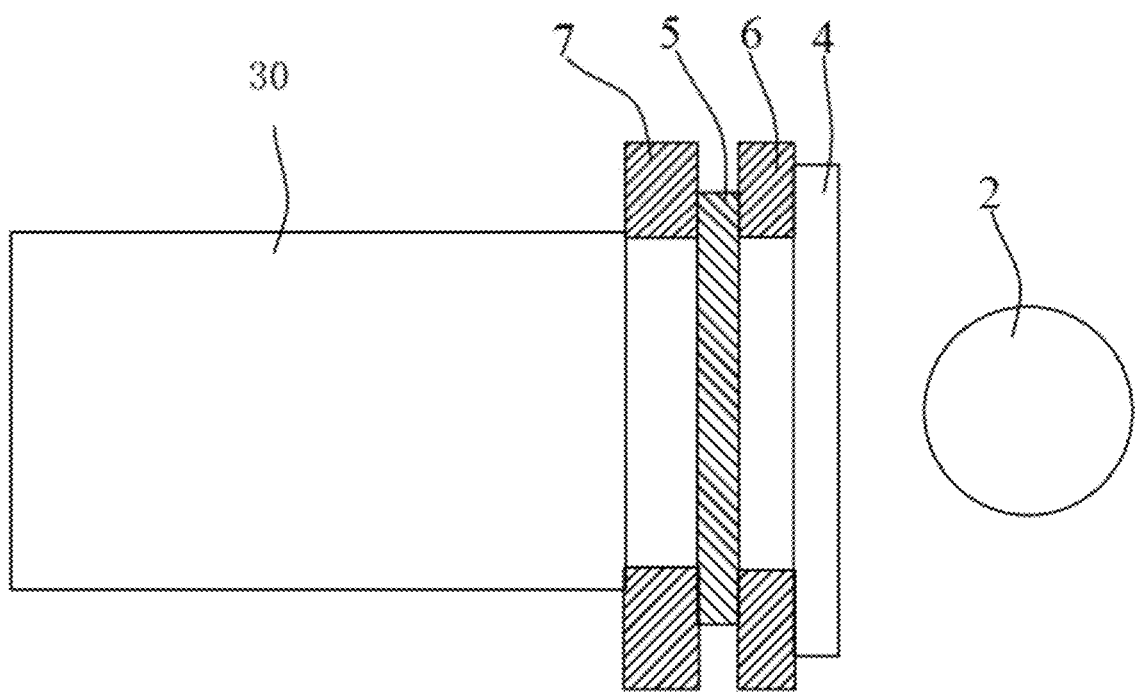
FIG. 19 is a schematic diagram of structures of a cold compress component, a heat insulation piece, a filter, a sealing member, and a light source according to an embodiment of this application.

In another embodiment, referring to FIG. 19, the first optical element 4 is spaced apart from the second optical element 5, the second optical element 5 is spaced apart from the cold compress component 30, the first sealing member 6 is disposed between the first optical element 4 and the second optical element 5, and a second sealing member 7 is disposed between the second optical element 5 and the cold compress component 30, that is, the filter 51 is separately spaced apart from the lens 32 and the heat insulation piece 41, the first sealing member 6 seals a gap between the heat insulation piece 41 and the filter 51, and the second sealing member 7 seals a gap between the filter 51 and the lens 32, to ensure that external hot air does not enter space between the heat insulation piece 41 and the lens 32.

Figure 20:
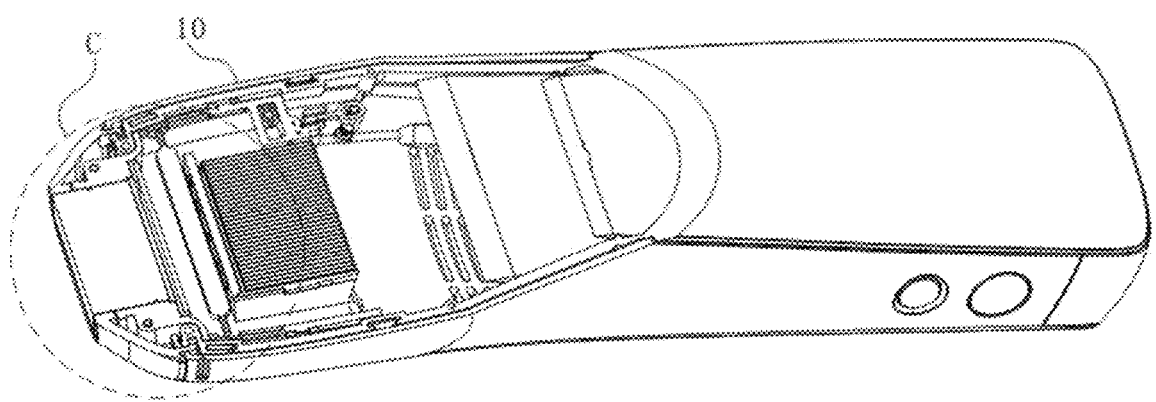
FIG. 20 is a schematic diagram of another internal structure of a beauty instrument according to an embodiment of this application.
Figure 21:
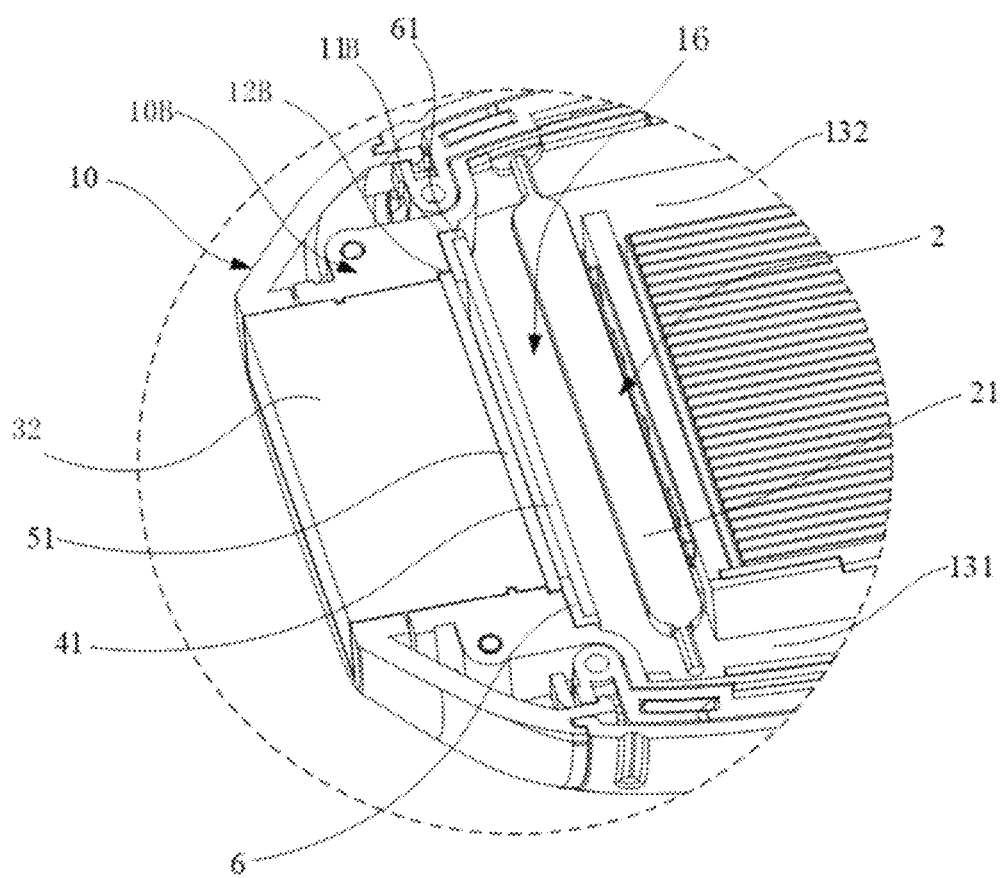
FIG. 21 is a schematic enlarged view at C in FIG. 20.
Figure 22:
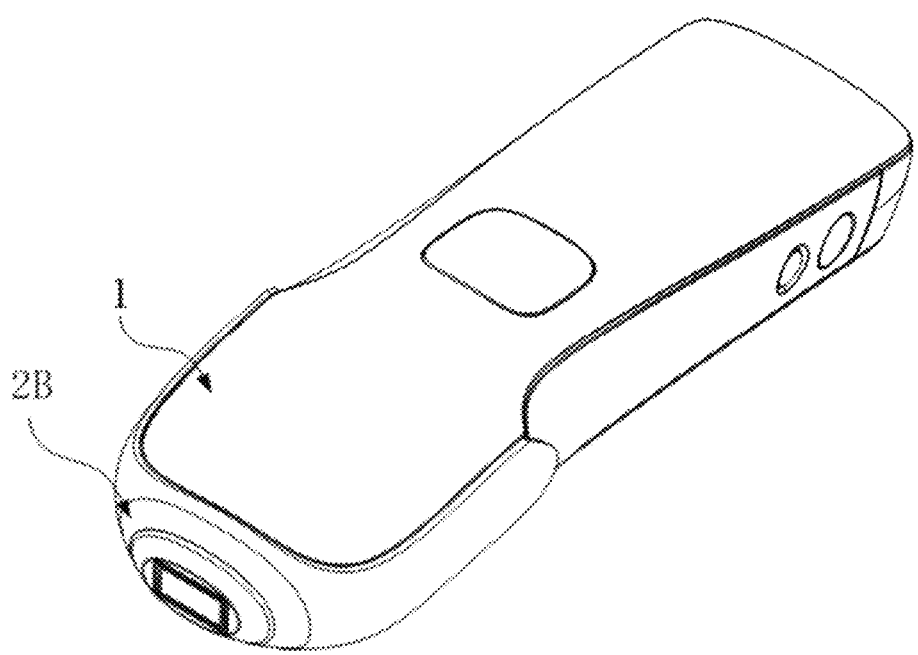
FIG. 22 is a schematic diagram of a structure of a beauty instrument according to an embodiment of this application.
Figure 23:
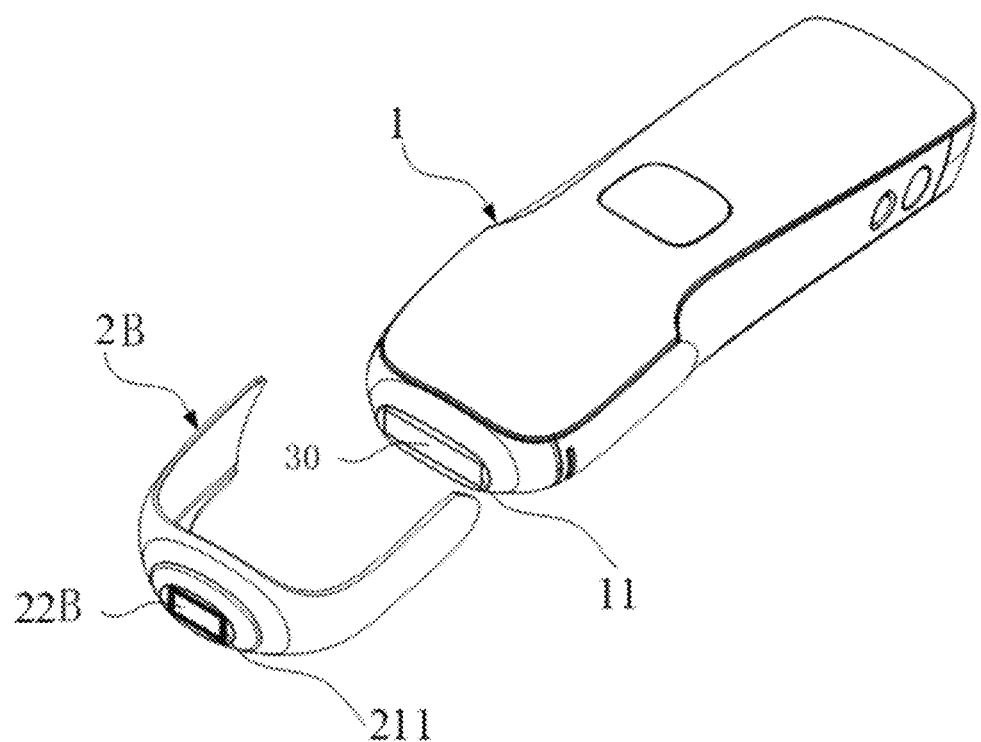
FIG. 23 is a schematic diagram of an exploded structure of a beauty instrument according to an embodiment of this application.

In some embodiments, referring to FIG. 20 and FIG. 21, the housing 10 has a mounting structure inside, configured to mount the heat insulation piece 41 and the filter 51. Optionally, the housing 10 includes a middle frame 10B, a first step part 11B is formed in the middle frame 10B, and the first step part 11B is disposed on a side that is of the cold compress component 30 and that faces the light source 2. An edge part of the heat insulation piece 41 is disposed in the first step part 11B, and separates inner space of the middle frame 10B into first space used to mount the light source 2 and second space used to mount the cold compress component 30, to block, out of the second space, heat radiated by the light source 2 in the first space, thereby reducing impact of the heat of the light source 2 on the cold compress component 30 in the second space. Optionally, a cross-section of the heat insulation piece 41 is greater than a cross-section of the cold compress component 30. When the heat insulation piece 41 is mounted at the first step part 11B, the heat insulation piece 41 totally covers the cold compress component 30, to block heat emitted by the light source.

Optionally, a second step part 12B is further formed in the middle frame 10B of the housing 10, and the second step part 12B is disposed on a side that is of the heat insulation piece 41 and that faces the cold compress component 30. The second step part 12B in this embodiment has a groove structure, and the groove of the second step part 12B matches a shape of the filter 51, to limit and fasten the filter 51.

Optionally, the heat insulation piece 41 in this embodiment is mounted at the first step part 11B by using the first sealing member 6. The first sealing member 6 is disposed in a shape of a square ring, and one side that is of the first sealing member 6 and that faces the cold compress component 30 is attached to both the first step part 11B and an end face of the filter 51. A third step part 61 is formed on the other side that is of the first sealing member 6 and that faces away from the cold compress component 30, and an edge part of the heat insulation piece 41 is disposed at the third step part 61. The third step part 61 has a groove that matches a shape of the heat insulation piece 41, to limit and fasten the heat insulation piece 41. The first sealing member 6 in this embodiment is elastic, has a cushion effect on the filter 51 and the heat insulation piece 41, and can protect the filter 51 and the heat insulation piece 41 from being affected by an external environment. An optical element closer to the lens 32 is protected to a largest extent. For example, when the hair removal instrument collides, because the first sealing member 6 is elastic and has a cushion effect on the filter 51 and the heat insulation piece 41, rigid collision between the filter 51 and the cold compress component 30 is avoided, and the filter 51 and the heat insulation piece 41 are protected.

In some embodiments, a projection region of the cold compress component 30 in the light exit direction is retracted in a projection region of the second optical element 5 in the light exit direction, and the projection region of the second optical element 5 in the light exit direction is retracted in a projection region of the first optical element 4 in the light exit direction. That is, cross-sectional areas of the cold compress component 30, the second optical element 5, and the first optical element 4 successively increase, to ensure that light passing through the cold compress component is not blocked by the first optical element 4 and the second optical element 5.

Still referring to FIG. 18 and FIG. 21, in some embodiments, to further reduce heat, a first gas flow channel 16 is formed in the housing 10, the first gas flow channel 16 is disposed on a side that is of the heat insulation piece 41 and that is close to the light source 2, and the light source 2 is disposed in the first gas flow channel 16. The first gas flow channel 16 is configured to dissipate heat for the light source 2 and the heat insulation piece 41. Specifically, the light source 2 is a lamp tube, the lamp tube is disposed in a width direction of the housing 10, and the lamp tube is parallel to and spaced apart from the heat insulation piece 41. One side of the heat insulation piece 41 forms a side wall of the first gas flow channel 16. The lamp tube is disposed at a distance from a bottom plate of the housing 10, so that the lamp tube is suspended in the first gas flow channel 16. This helps dissipate heat for the lamp tube. Optionally, the first gas flow channel 16 extends in a length direction of the lamp tube, a gas inlet 131 and a gas outlet 132 are respectively disposed at two ends of the first gas flow channel 16, a fan (not shown in the figure) is disposed at the gas inlet 131, and the gas outlet 132 communicates with the outside of the housing 10. The fan may blow out cooling air. The cooling air is blown into the first gas flow channel 16 through the gas inlet 131, and takes away heat of the lamp tube in the first gas flow channel 16 and the heat insulation piece 41. Finally, the air used for heat dissipation is discharged from the gas outlet 132 of the first gas flow channel 16 to the outside of the housing 10, to complete heat dissipation on the lamp tube and the heat insulation piece 41, and reduce temperatures of the lamp tube and the heat insulation piece 41. Optionally, a reflector body edge that is of the reflector 22 and that faces the heat insulation piece 41 is notched to form a second opening 211, and the second opening 211 communicates with the first gas flow channel 16. The second opening 211 is in a shape of a long strip, and extends toward two opposite sides of the reflector 22. The cooling air is blown from the first gas flow channel 16 to the heat insulation piece 41, and is discharged from the housing 10 through the second opening 221, thereby reducing heat of a side that is of the heat insulation piece 41 and that faces the light source 2.

Still referring to FIG. 18, in some embodiments, to further improve user experience, the cold compress component 30 includes a lens 32 configured to be in contact with the human skin and a semiconductor cooling plate 31, the semiconductor cooling plate 31 has a cooling surface and a heating surface, and the cooling surface of the semiconductor cooling plate 31 is in contact with the lens 32. The lens 32 may be a sapphire. During working, the cooling surface of the semiconductor cooling plate 31 is attached to the lens 32, to conduct a cooling airflow to the lens 32. The lens 32 is in contact with the human body, to conduct the cooling airflow to the skin, so that an icy feeling is generated on the skin, thereby reducing a burning feeling generated during hair removal, and improving user experience.

Cooling working of the semiconductor cooling plate 31 generates heat, and heat dissipation needs to be performed on the semiconductor cooling plate 31. Optionally, a heat sink 8 is disposed on a side that is of the light source 2 and that faces away from the light exit direction, and the heat sink 8 is connected to the heating surface of the semiconductor cooling plate 31 by using a thermally conductive member 9. The heat sink 8 in this embodiment is configured to dissipate heat for the semiconductor cooling plate 31. Specifically, a thermally conductive member 9 is connected between the heat sink 8 and the semiconductor cooling plate 31. One end of the thermally conductive member 9 is in contact with the heating surface of the semiconductor cooling plate 31, and the other end thereof is in contact with the heat sink 8. Heat generated by the heating surface of the semiconductor cooling plate 31 is conducted to the heat sink 8 by using the thermally conductive member 9, and the heat sink 8 brings the heat out of the housing 10, to complete heat dissipation on the semiconductor cooling plate 31.

Referring to FIG. 22 to FIG. 29, a beauty instrument provided in an embodiment of this application includes a beauty instrument body 1 and a beauty instrument accessory head 2B. The beauty instrument accessory head 2B is configured to be used in conjunction with the beauty instrument body 1. The beauty instrument body 1 may be the beauty instrument in the foregoing embodiment. The beauty instrument body 1 includes a housing 10, one end of the housing 10 is provided with a first light outlet 11, and one end of the beauty instrument body 1 is provided with a cold compress component 30.

The beauty instrument accessory head 2B includes:
an outer cover 210, configured to be detachably connected to the beauty instrument body 1, and including a contact outer surface and a connection outer surface;
a conductive member 22B, disposed on the outer cover 210, and including a first end face exposed to the contact outer surface and a second end face exposed to the connection outer surface, where the first end face is configured to be in contact with the human skin, and the second end face is configured to be in contact with the cold compress component 30 when the outer cover 210 is connected to the beauty instrument body 1; and
an elastic member 22C, disposed between the outer cover 210 and the conductive member 22B, where one end of the elastic member 22C acts on the outer cover 210, and the other end thereof acts on the conductive member 22B toward the second end face, so that the conductive member 22B is attached to the cold compress component 30 when the outer cover 210 is connected to the beauty instrument body 1.

The beauty instrument body 1 in this embodiment is a beauty instrument that can independently perform skin care, and may be specifically a hair removal instrument. The beauty instrument body 1 includes a handheld part 14, and the handheld part 14 is disposed with a specific curvature, conforms to ergonomics, and is convenient for the user to hold. The beauty instrument body 1 may emit light used to care for the human skin. The light may be intense pulse light or laser light. The laser light and the intense pulse light can stimulate hair follicles without damaging normal skin tissues, so that the hair follicles absorb light energy to change structures of the hair follicles, thereby achieving a hair removal effect. Optionally, the beauty instrument body 1 includes a light source (not shown in the figure) for emitting light. The light source may be a laser lamp, a xenon lamp, an LED lamp, or the like. Light emitted by the light source is emitted from the cold compress component 30 at one end of the beauty instrument body 1 to the skin, to remove hair from the skin. During hair removal, the light acts on the human skin, and a slight burning feeling may be generated on the skin. In some embodiments, the cold compress component 30 includes a cold compress member 121 and a semiconductor cooling plate 31. The cold compress 121 may be a lens 32, the semiconductor cooling plate 31 has a cooling surface and a heating surface, and the cooling surface of the semiconductor cooling plate 31 is in contact with the cold compress member 121. During working, the cooling surface of the semiconductor cooling plate 31 is attached to the cold compress member 121, to conduct a generated cooling airflow to the cold compress member 121. The cold compress member 121 is in contact with the human body, to conduct the cooling airflow to the skin, so that an icy feeling is generated on the skin, thereby reducing a burning feeling generated during hair removal, and improving user experience. The cold compress member 121 may be a lens such as a sapphire. The sapphire has good thermal conductivity and heat dissipation performance. When light passes through the sapphire, the sapphire can absorb heat quickly and transfer the heat to the outside of the hair removal instrument. In this way, the sapphire can quickly cool the skin surface, reduce heat transferred to deep skin layers, and reduce a degree of the burning feeling.

It may be understood that, in some other embodiments, the cold compress member 121 may further be a non-transparent structural member such as metal or ceramic. Specifically, the beauty instrument body 1 further includes the first light outlet 11 for emitting light, and the cold compress member 121 is disposed around the light outlet. When the hair removal instrument removes hair, the light outlet is attached to the skin, light emitted by the light source is radiated to the human skin by using the first light outlet 11, and the cold compress member 121 soothes the skin around the light outlet, thereby relieving the burning feeling.

When hair removal needs to be performed on different parts of the body, the accessory head generally needs to be replaced. After the accessory head is replaced for the hair removal instrument, because the accessory head is not provided with a cold compress component, a cooling effect thereof on the skin is difficult to meet a user requirement. In this case, the beauty instrument accessory head 2B in this embodiment is provided with the conductive member 22B and the elastic member 22C. The conductive member 22B includes the first end face exposed to the contact outer surface of the outer cover 210 and the second end face exposed to the connection outer surface of the outer cover 210. The elastic member 22C enables the second end face of the conductive member 22B to be attached to the cold compress member 121 of the cold compress component 30. Specifically, the elastic member 22C is disposed between the outer cover 210 and the conductive member 22B. When the beauty instrument accessory head 2B is connected to the beauty instrument body 1, one end of the elastic member 22C acts on the outer cover 210, and the other end thereof acts on the conductive member 22B toward the second end face of the conductive member 22B, so that the conductive member 22B is attached to the cold compress member 121. The conductive member 22B may be metal or ceramic disposed around the light outlet on the outer cover 210, or a material that can conduct a cooling airflow and that is disposed in the first light outlet 11, for example, a sapphire. The sapphire may transmit light, and has a better effect of conducting the cooling airflow. In this embodiment, a sapphire disposed in the first light outlet 11 is used as an example for description of both the cold compress member 121 and the conductive member 22B. During hair removal, a cooling airflow generated by the semiconductor cooling plate 31 of the beauty instrument body 1 acts on the skin successively through the cold compress member 121 and the conductive member 22B, to cool the skin surface. Because the elastic member 22C acts on the conductive member 22B toward the second end face of the conductive member 22B, the conductive member 22B is always subjected to a force that points to the connection outer surface of the outer cover, so that the conductive member 22B can be attached to the cold compress member 121, that is, the two sapphires are tightly attached to each other. This helps conduct the cooling airflow to the skin, thereby reducing a skin temperature, and improving a cooling effect of the beauty instrument on the skin and user experience.

Figure 24:
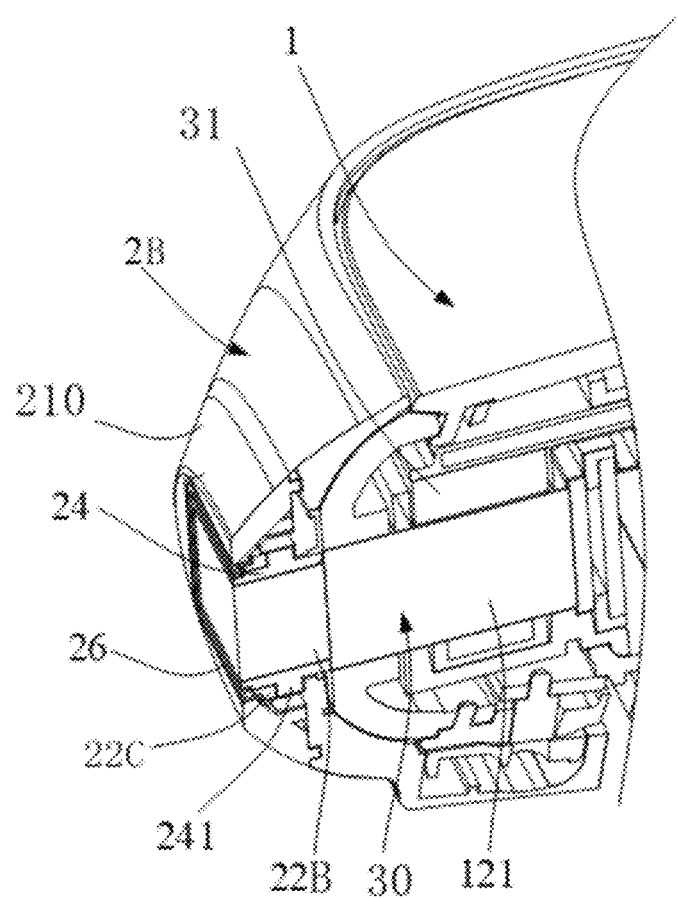
FIG. 24 is a schematic diagram of a partial internal structure of a beauty instrument according to an embodiment of this application.
Figure 25:
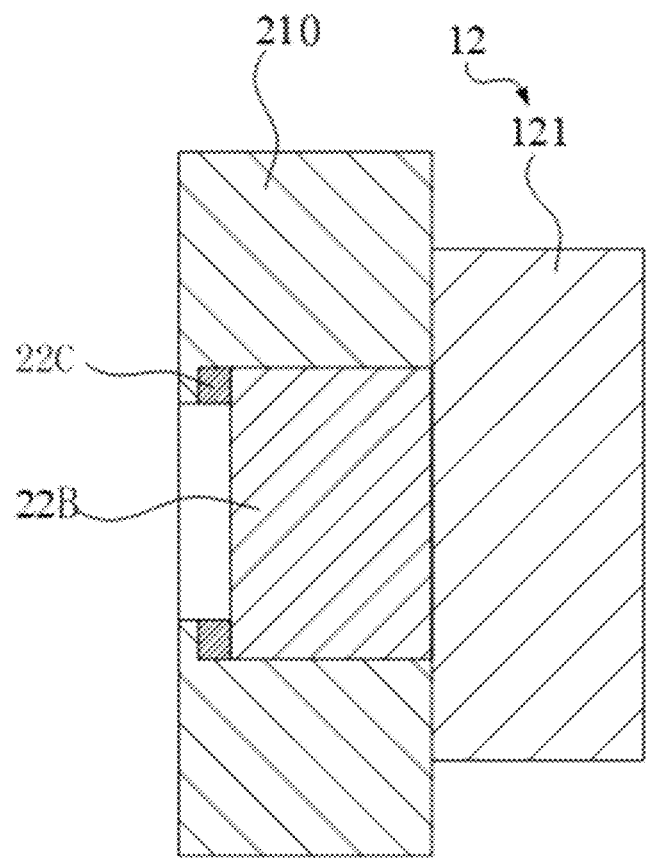
FIG. 25 is a schematic diagram of structures of a cold compress component, a conductive member, an elastic member, and an outer cover according to an embodiment of this application.
Figure 26:
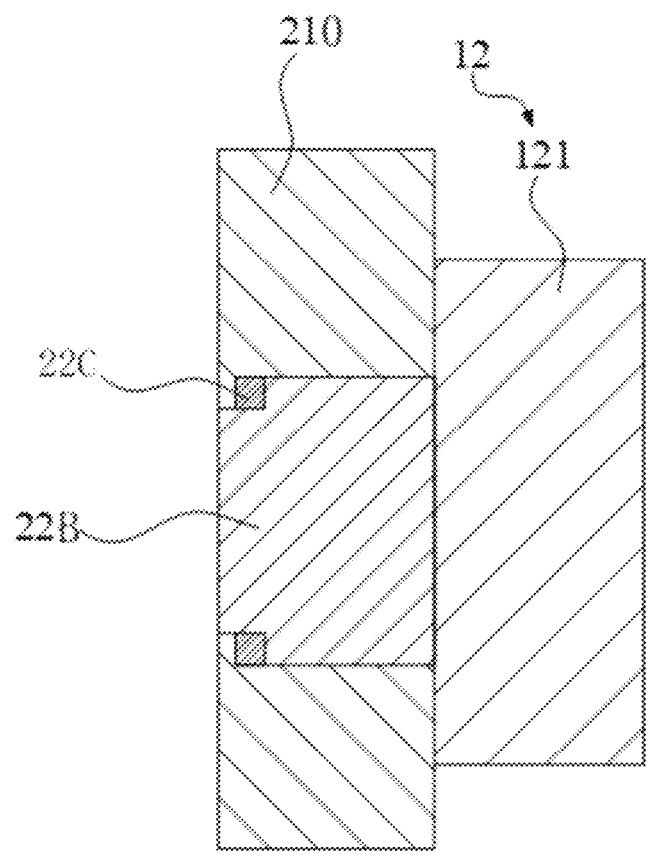
FIG. 26 is a schematic diagram of structures of a cold compress component, a conductive member, an elastic member, and an outer cover according to another embodiment of this application.

Referring to FIG. 24 to FIG. 26, the elastic member 22C in this embodiment is configured to apply an elastic force to the conductive member 22B, so that the conductive member 22B is continuously attached to the cold compress member 121. In addition, when accidental collision occurs, the elastic member 22C has a cushion effect, so that rigid collision between the conductive member 22B and the cold compress member 121 is avoided, and two light guiding elements are protected. The elastic member 22C may be a spring, rubber, an elastic polymer, or the like. For example, the elastic member 22C is an annular rubber structure. The following describes a manner of disposing the elastic member 22C.

Figure 29:
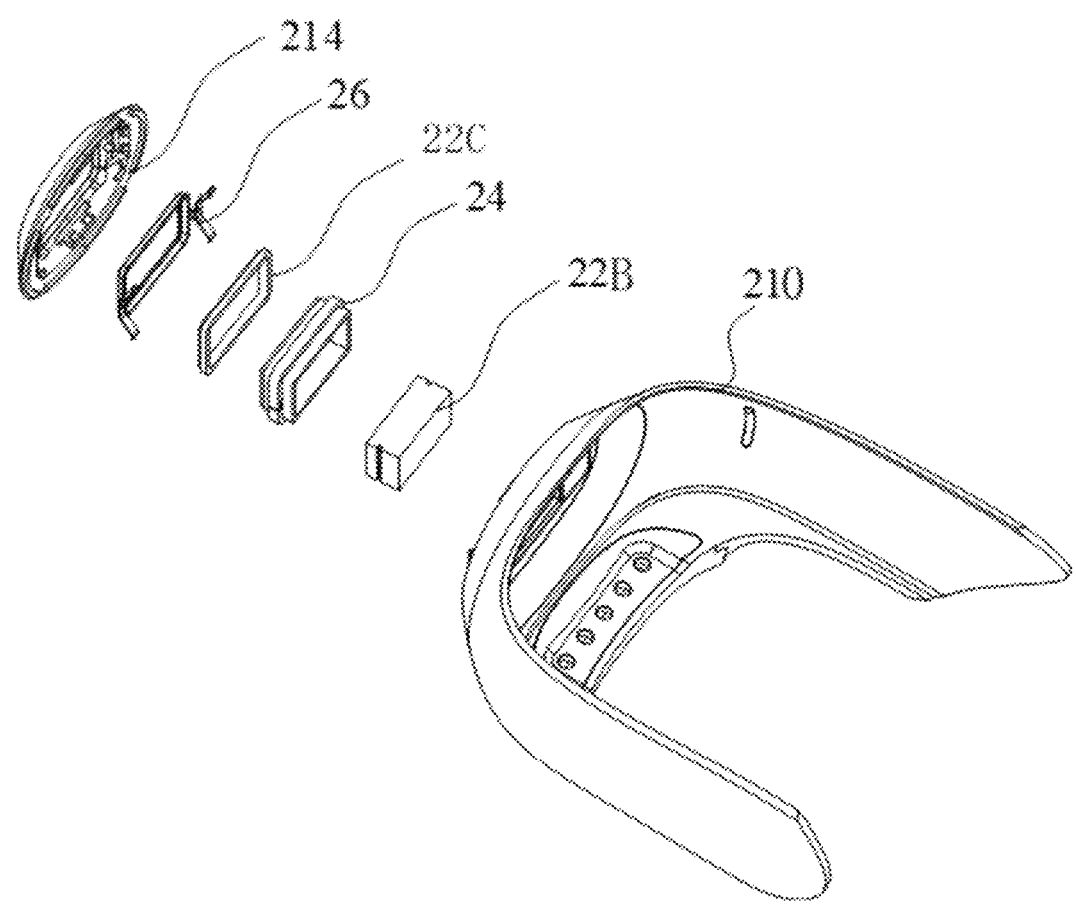
FIG. 29 is a schematic diagram of an exploded structure of a beauty instrument accessory head according to an embodiment of this application.

As shown in FIG. 24 and FIG. 29, in some embodiments, the beauty instrument accessory head 2B further includes a mounting frame 24 configured to mount the conductive member 22B. The mounting frame 24 surrounds the conductive member 22B, a flange part 241 is formed on an outer side of the mounting frame 24, the elastic member 22C is disposed on a side that is of the flange part 241 and that is away from the cold compress component 30, one end of the elastic member 22C abuts on the flange part 241, and the other end thereof acts on the outer cover 210. The conductive member 22B in this embodiment is disposed in a shape of a rectangular block. An inner frame of the mounting frame 24 is sleeved on the conductive member 22B, and the flange part 241 on the outer side of the mounting frame 24 is clamped with the outer cover 210, so that the conductive member 22B is mounted in the outer cover 210. The elastic member 22C is disposed on a side that is of the flange part 241 and that is away from the second end face of the conductive member 22B, and is pressed against between the flange part 241 and the outer cover 210. When the beauty instrument accessory head 2B is sleeved on the beauty instrument body 1, the conductive member 22B is attached to the cold compress member 121, the elastic member 22C is deformed and applies an elastic force to the conductive member 22B toward the second end face, and the conductive member 22B continuously extrudes the cold compress member 121 under the action of the elastic force, so that the conductive member 22B is more closely attached to the cold compress member 121.

As shown in FIG. 25, in another embodiment, at least a part of the elastic member 22C is disposed on the first end face of the conductive member 22B, at least one end of the elastic member 22C abuts on the conductive member 22B, and at least the other end thereof acts on the outer cover 210. At least one end of the elastic member 22C in this embodiment is pressed against between the first end face of the conductive member 22B and the outer cover 210. It may be understood that, in this embodiment, the elastic member 22C may be totally disposed on the first end face of the conductive member 22B, or only a part of the elastic member 22C may be disposed on the first end face of the conductive member 22B. Therefore, the elastic member 22C between the first end face of the conductive member 22B and the outer cover 210 may be deformed to apply a force to the conductive member 22B toward the second end face of the conductive member 22B. When the beauty instrument accessory head 2B is connected to the beauty instrument body 1, the conductive member 22B continuously extrudes the cold compress member 121 under the action of the force generated by the elastic member 22C, so that the conductive member 22B is more closely attached to the cold compress member 121.

As shown in FIG. 26, in still another embodiment, a step part that can accommodate the elastic member 22C is convexly disposed on an outer peripheral surface of the conductive member 22B, one end that is of the elastic member 22C and that faces the cold compress member 121 abuts on the step part, and the other end thereof acts on the outer cover 210. The elastic member 22C in this embodiment abuts between the step part and the outer cover 210. When the beauty instrument accessory head 2B is connected to the beauty instrument body 1, the conductive member 22B is attached to the cold compress member 121, the elastic member 22C is deformed and applies an elastic force to the step part toward the cold compress member 121, and the conductive member 22B continuously extrudes the cold compress member 121 under the action of the elastic force, so that the conductive member 22B is more closely attached to the cold compress member 121.

This application further provides a beauty instrument. The beauty instrument includes a beauty instrument body 1 and the beauty instrument accessory head 2B described in the foregoing embodiment. The beauty instrument accessory head 2B is sleeved on the beauty instrument body 1. A cold compress component 30 is disposed in a first light outlet 11 or a cold compress component 30 is disposed on an outer periphery of a first light outlet 11. A second light outlet 211 is formed on an outer cover 210. A conductive member 22B is disposed in the second light outlet 211 or a conductive member 22B is disposed on an outer periphery of the second light outlet 211. A size of the second light outlet 211 is different from a size of the first light outlet 11.

It may be understood that, when the cold compress component 30 of the beauty instrument is disposed in the first light outlet 11, the conductive member 22B of the beauty instrument accessory head 2B is disposed in the second light outlet 211. When the cold compress component 30 of the beauty instrument is disposed on the outer periphery of the first light outlet 11, the conductive member 221B of the beauty instrument accessory head 2B is also correspondingly disposed on the outer periphery of the second light outlet 211. In this way, when the beauty instrument accessory head 2B is sleeved on the beauty instrument body 1, the cold compress component 30 and the conductive member 22B may be mutually attached to implement cold conduction.

The second light outlet 211 whose size is different from that of the first light outlet 11 of the beauty instrument body 1 is disposed on the beauty instrument accessory head 2B in this embodiment, to meet hair removal requirements of different body parts of a user. Specifically, the second light outlet 211 of the beauty instrument accessory head 2B directly faces the first light outlet 11, and light emitted by the beauty instrument body 1 acts on the human skin through the conductive member 22B in the second light outlet 211, to remove hair from the skin. Because the size of the second light outlet 211 is different from the size of the first light outlet 11, the second light outlet 211 may be used for hair removal on different body parts. For example, a hair removal instrument with a larger light outlet may cover a larger skin area, to accelerate a hair removal speed, so that the hair removal instrument is applicable to the leg, the back, and the like. This design can also reduce stimulation and discomfort to the skin. A reason is that light distribution over a large area can disperse light energy more evenly. A hair removal instrument with a smaller light outlet is suitable for a small and hard-to-reach skin region such as the underarm and various parts of the face. This design can help the user more accurately target a to-be-treated hair region, thereby reducing unnecessary exposure to the surrounding skin, and avoiding unnecessary stimulation to the surrounding skin. Therefore, the sizes of the first light outlet 11 and the second light outlet 211 of the hair removal instrument in this embodiment are different, so that hair removal requirements of different skin parts can be met, and more comfortable and effective hair removal experience can be provided. Optionally, the second light outlet 211 in this embodiment is less than the first light outlet 11.

In addition, the beauty instrument accessory head 2B in this embodiment is detachably sleeved on the beauty instrument body 1, so that the user can easily replace the beauty instrument accessory head 2B for skin care. Specifically, the outer cover 210 of the beauty instrument accessory head 2B extends in directions of two sides of the second light outlet 211 to form two connection arms 212, and the two connection arms 212 are clamped on two sides of the beauty instrument body 1. For example, a connection manner between the connection arm 212 and the beauty instrument body 1 may be a snap-in, insertion, or magnetic connection, so that a structure is compact and easy to carry.

In some embodiments, the two connection arms 212 are elastic connection arms 212, and a volume of clamping space formed between the two elastic connection arms 212 is less than a connection end of the beauty instrument body 1. Because the connection arm 212 is elastic, when the connection end of the beauty instrument body 1 is inserted into the clamping space, the clamping space expands, and elastic forces of the two connection arms 212 act on the two sides of the beauty instrument body 1, to clamp the beauty instrument body 1. Optionally, the two connection arms 212 are clamped on two sides of the beauty instrument body 1 in a width direction.

Figure 27:
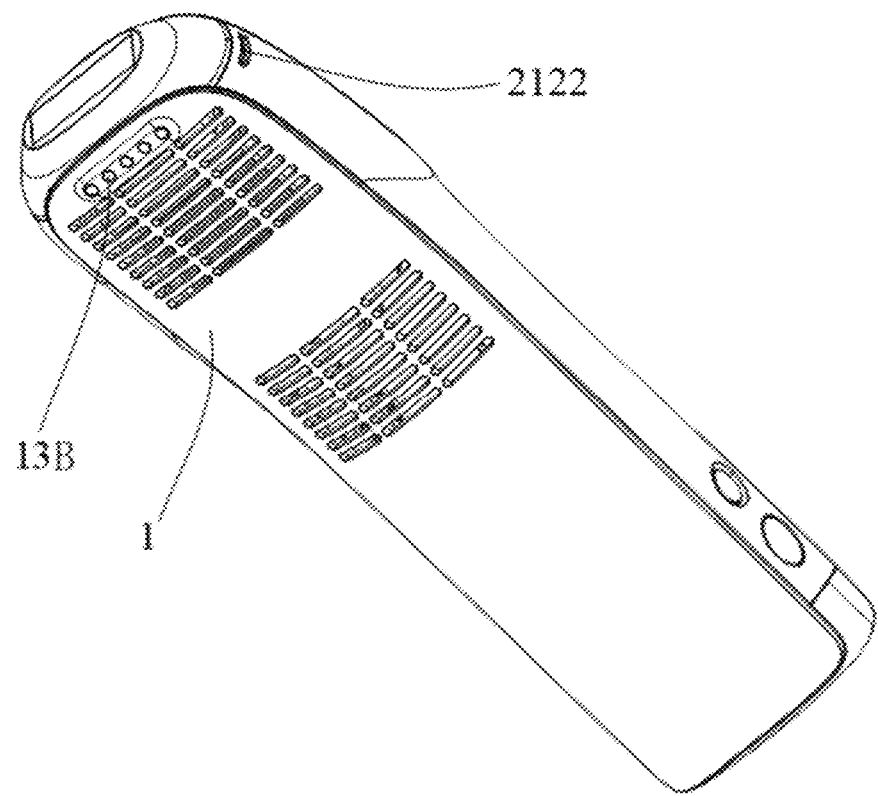
FIG. 27 is a schematic diagram of a structure of a beauty instrument body according to an embodiment of this application.
Figure 28:
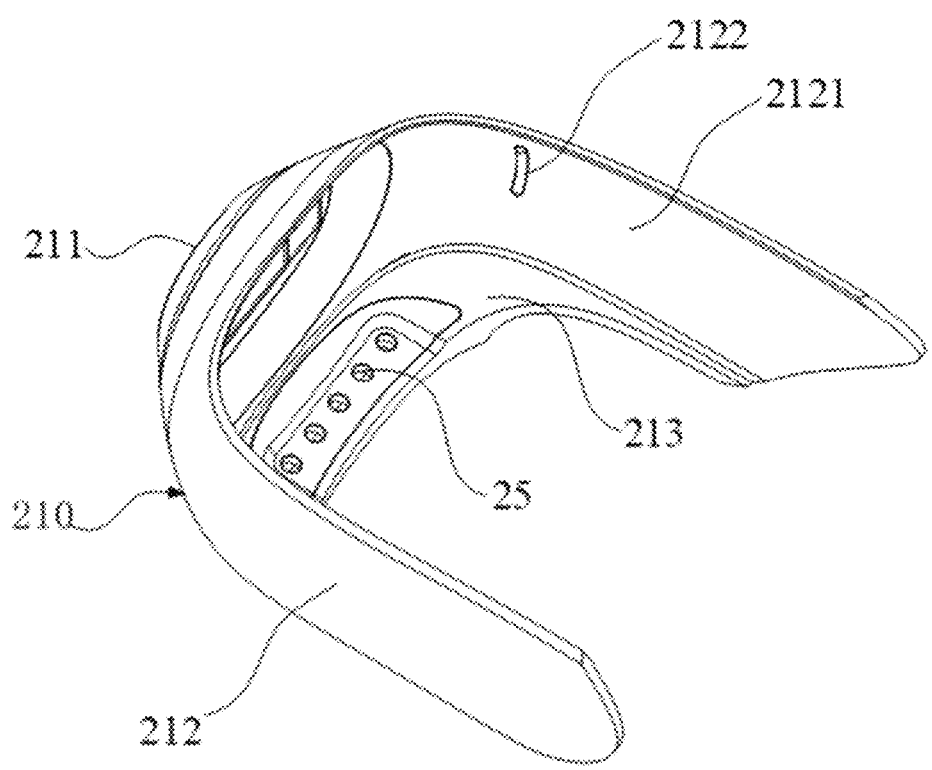
FIG. 28 is a schematic diagram of a structure of a beauty instrument accessory head according to an embodiment of this application.

In some embodiments, still referring to FIG. 27 and FIG. 28, a snap-fit structure 2122 is disposed between the connection arm 212 and the beauty instrument body 1, and the connection arm 212 is detachably mounted on the beauty instrument body 1 by using the snap-fit structure 2122.

Further, the snap-fit structure 2122 includes a boss disposed on an inner side of the connection arm 212 and a groove disposed on an outer side of the beauty instrument body 1; or the snap-fit structure 2122 includes a groove disposed on an inner side of the connection arm 212 and a boss disposed on an outer side of the beauty instrument body 1.

In this embodiment, a connection manner between the beauty instrument accessory head 2B and the beauty instrument body 1 is a snap-in connection, and the snap-fit structure 2122 is disposed between the connection arm 212 and the beauty instrument body 1. Specifically, a boss is disposed on an inner side of at least one connection arm 212, a groove is correspondingly disposed on an outer side of the beauty instrument body 1, or a groove is disposed on an inner side of at least one connection arm 212, a boss is correspondingly disposed on an outer side of the beauty instrument body 1. The groove matches the boss. When the beauty instrument accessory head 2B is sleeved on the beauty instrument body 1, the boss is snapped into the groove, to implement the snap-in connection between the connection arm 212 and the beauty instrument body 1.

In some embodiments, an end that is of a side wall of the beauty instrument body 1 and that is close to the beauty instrument accessory head 2B forms a first curved surface, and sides that are of the two connection arms 212 and that are opposite to each other each are formed with a limiting slot 2121 for insertion of the side wall that is of the beauty instrument body 1 and that has the first curved surface. At least one inner surface of the limiting slot 2121 is a second curved surface adapted to the first curved surface.

In this embodiment, a connection manner between the beauty instrument accessory head 2B and the beauty instrument body 1 is an insertion connection. Specifically, an end that is of the side wall of the beauty instrument body 1 and that is close to the beauty instrument accessory head 2B forms a curved surface, and at least one inner surface of the limiting slot 2121 is also a curved surface, to be adapted to the side wall that is of the beauty instrument body 1 and that has a curved surface. When an end of the inner surface that is of the beauty instrument body 1 and that has a curved surface is inserted into the limiting slot 2121, the limiting groove 2121 has a guiding effect, to facilitate insertion of the beauty instrument body 1. Optionally, the outer cover 210 is further formed with a connection bottom plate 213, and the connection bottom plate 213 is connected between the two connection arms 212. After the beauty instrument body 1 is inserted into the limiting slot 2121, the connection bottom plate 213 may carry the beauty instrument body 1, thereby improving insertion reliability.

In some embodiments, a first magnetic member is disposed on the beauty instrument accessory head 2B, a second magnetic member is disposed at a corresponding location on the beauty instrument body 1, and the beauty instrument accessory head 2B is detachably mounted on the beauty instrument body 1 through mutual attraction between the first magnetic member and the second magnetic member; or
   the connection arm 212 is of a magnetic material, a second magnetic member is disposed on an outer side of the beauty instrument body 1, and the connection arm 212 is detachably mounted on the beauty instrument body 1 by using a magnetic effect.

In this embodiment, a connection manner between the beauty instrument accessory head 2B and the beauty instrument body 1 is a magnetic connection. Specifically, a first magnetic member is disposed on the beauty instrument accessory head 2B, and a second magnetic member is disposed on the beauty instrument body 1. When the beauty instrument accessory head 2B is sleeved on the beauty instrument body 1, the first magnetic member and the second magnetic member are mutually attracted, to implement the magnetic connection between the beauty instrument accessory head 2B and the beauty instrument body 1. Alternatively, the connection arm 212 of the beauty instrument accessory head 2B is of a magnetic material, and the second magnetic member directly attracts the connection arm 212. The magnetic material may be iron, an iron alloy, or the like, and the first magnetic member and the second magnetic member may be magnets.

Still referring to FIG. 27 and FIG. 28, in some embodiments, a first electrically conductive contact 25 is disposed on the beauty instrument accessory head 2B, a second electrically conductive contact 13B is disposed on the beauty instrument body 1, and when the beauty instrument accessory head 2B is sleeved on the beauty instrument body 1, the first electrically conductive contact 25 is in contact with and electrically connected to the second electrically conductive contact 13B.

In this embodiment, when the beauty instrument accessory head 2B is mounted on the beauty instrument body 1, the beauty instrument accessory head 2B is electrically connected to the beauty instrument body 1, and the beauty instrument accessory head 2B obtains electric energy of the beauty instrument body 1, to perform skin care. Specifically, the first electrically conductive contact 25 is disposed on the beauty instrument accessory head 2B, the second electrically conductive contact 13B is disposed on the beauty instrument body 1, and when the beauty instrument accessory head 2B is sleeved on the beauty instrument body 1, the first electrically conductive contact 25 is in contact with and electrically connected to the second electrically conductive contact 13B, so that the beauty instrument accessory head 2B is electrically connected to the beauty instrument body 1.

Optionally, the first electrically conductive contact 25 includes a plurality of elastic electrodes disposed at intervals, and the second electrically conductive contact 13B includes a plurality of elastic electrodes disposed at intervals. When the beauty instrument accessory head 2B is sleeved on the beauty instrument body 1, the elastic electrodes of the first electrically conductive contact 25 are in contact with the elastic electrodes of the second electrically conductive contact 13B through extrusion in a one-to-one correspondence, so that the beauty instrument accessory head 2B is electrically connected to the beauty instrument body 1.

Optionally, the first electrically conductive contact 25 is disposed on the connection bottom plate 213, and the second electrically conductive contact 13B is disposed on a surface that is of the beauty instrument body 1 and that faces the connection bottom plate 213.

Optionally, the connection bottom plate 213 is connected between the two connection arms 212 of the beauty instrument accessory head 2B, and forms accommodation space with the two connection arms 212. When the beauty instrument accessory head 2B is sleeved on the beauty instrument body 1, the beauty instrument body 1 partially extends into the accommodation space, so that the first electrically conductive contact 25 on the connection bottom plate 213 is in contact with and electrically connected to the second electrically conductive contact 13B on the bottom surface of the beauty instrument body 1.

Still referring to FIG. 29, in some embodiments, the beauty instrument accessory head 2B further includes a detection member 26 disposed at the second light outlet 211, and the detection member 26 is electrically connected to the first electrically conductive contact 25, and surrounds the conductive member 22B to detect the human skin.

The detection member 26 in this embodiment is configured to detect the human skin. Specifically, the detection member 26 surrounds the conductive member 22B, and is electrically connected to the second electrically conductive contact 13B. When the beauty instrument accessory head 2B is mounted on the beauty instrument body 1, the conductive member 22B directly faces the cold compress member 121, and the detection member 26 is electrically connected to the beauty instrument body 1. When the detection member 26 is close to or in contact with the skin, the detection member 26 sends a working signal to the beauty instrument body 1, so that the beauty instrument body 1 emits light. The light is exported to the human skin through the conductive member 22B, to remove hair from the skin.

Still referring to FIG. 24, in some embodiments, the elastic member 22C abuts between the detection member 26 and the flange part 241 of the mounting frame 24, and the detection member 26 is fixedly mounted at the second light outlet 211. When the beauty instrument accessory head 2B is sleeved on the beauty instrument body 1, the conductive member 22B is attached to the cold compress member 121, the elastic member 22C is deformed and applies an elastic force to the conductive member 22B toward the cold compress member 121, and the conductive member 22B continuously extrudes the cold compress member 121 under the action of the elastic force, so that the conductive member 22B is more closely attached to the cold compress member 121.

Yet another embodiment of this application provides a beauty instrument. Referring to FIG. 1, the beauty instrument includes at least a housing 10, a beauty component, and a heat dissipation component. The beauty component and the heat dissipation component are disposed in the housing 10. The beauty component is configured to care for a surface of the human skin. During working, the beauty component generates heat in the housing 10, and the heat dissipation component is configured to discharge the heat in the housing 10 to the outside, to prevent the housing 10 from being heated or scalded because the heat is accumulated.

As shown in FIG. 2 and FIG. 3, an air inlet hole 13 and several air outlet holes 12 are disposed on the housing 10, a heat dissipation component generally includes an airflow generation apparatus and a heat sink 42, and the heat dissipation component is disposed in the housing 10, and includes an airflow generation apparatus and a heat sink 42. The airflow generation apparatus includes an air inlet and an air outlet, the air inlet of the airflow generation apparatus communicates with the air inlet hole 13, and the heat sink 42 has a first air outlet K1 communicating with the air outlet hole 12 and an air inlet K2 communicating with the air outlet of the airflow generation apparatus. The air outlet of the airflow generation apparatus communicates with the heat sink 42. After a part of cooling air generated by the airflow generation apparatus flows through the heat sink 42, the cooling air takes away heat on the heat sink 42, and is discharged through the air outlet hole 12 disposed on the housing 10. It may be understood that, when the airflow generation apparatus works, an external cooling airflow flows from the outside into the housing 10 through the air inlet hole 13 disposed on the housing 10, and then enters the airflow generation apparatus.

Further, with reference to FIG. 4 to FIG. 8, in this embodiment, a first gas flow channel 16 is disposed in the housing 10, and the first gas flow channel 16 includes a gas inlet and a gas outlet. The beauty component is disposed in the housing 10 and is located in the first gas flow channel 16. The air outlet of the airflow generation apparatus further communicates with the gas inlet of the first gas flow channel 16, and the gas outlet of the first gas flow channel 16 communicates with the air outlet hole 12. After a part of cooling air generated by the airflow generation apparatus enters the first gas flow channel 16 through the gas inlet of the first gas flow channel 16, the cooling air flows out from the gas outlet to the air outlet hole 12 to be discharged. After another part of cooling air generated by the airflow generation apparatus enters the heat sink 42 through the air inlet K2 of the heat sink 42, the cooling air flows out from the first air outlet K1 to the air outlet hole 12 to be discharged. The housing 10 has a top surface, a bottom surface, and a side surface, and all the air outlet holes 12 are located on the top surface of the housing 10, or are located on the bottom surface of the housing 10. The air outlet holes 12 are neither disposed on a side surface of the housing 10, nor are separately disposed on two surfaces of the housing 10. Therefore, when the beauty instrument is used, all the air outlet holes 12 may face away from the user. It may be understood that, in some other embodiments, the first gas flow channel 16 is not disposed in the beauty instrument. In this case, the cooling air generated by the airflow generation apparatus all passes through the heat sink 42, and then flows out from the first air outlet K1 to the air outlet hole 12.

The beauty instrument in this application includes the first gas flow channel 16 and the heat sink. After a part of cooling air generated by the airflow generation apparatus passes through the first gas flow channel 16, the cooling air flows out from the gas outlet of the first gas flow channel 16 to the air outlet hole on the housing. After another part of cooling air generated by the airflow generation apparatus passes through the heat sink, the cooling air flows out from the first air outlet of the heat sink to the air outlet hole on the housing, thereby improving a heat dissipation effect inside the beauty instrument. In addition, all the air outlet holes on the housing are located on a same surface such as the top surface or the bottom surface of the housing. Therefore, in a process in which the user uses the beauty instrument, regardless of which hand with which the user holds the beauty instrument, the air outlet holes of the beauty instrument do not face the user. Therefore, a burning risk of the user can be reduced.

For example, all the air outlet holes 12 are located on the bottom surface of the housing 10. When the user holds the beauty instrument with the hand for skin care, the user may enable the bottom surface of the housing 10 to face outward for care, and the air outlet holes 12 face away from the user, so that no heat is discharged toward the human body. For example, when the user holds the beauty instrument with the left hand, the thumb holds the top surface of the housing 10, and the remaining four fingers hold the bottom surface of the housing 10, so that the cold compress component 30 is in contact with the human skin. When the user holds the beauty instrument with the right hand, the thumb still holds the top surface of the housing 10, and the remaining four fingers hold the bottom surface of the housing 10, so that the cold compress component 30 is in contact with the human skin. In this way, regardless of which hand with which the user holds the beauty instrument, the air outlet holes of the beauty instrument do not face the user.

A person skilled in the art may integrate or combine different embodiments or examples and characteristics of different embodiments or examples described in this specification, provided that they do not conflict with each other.

The foregoing descriptions are merely some embodiments of this application, and are not intended to limit the protection scope of this application either in terms of text or the accompanying drawings. Any equivalent structure transformation that is in accordance with the overall idea of this application and that is made according to the content in the specification and the accompanying drawings of this application, or an application of the content in the specification and the accompanying drawings of this application directly/indirectly to another related technical field, shall fall within the protection scope of this application.

What is claimed is:
1. A beauty instrument, comprising:
 a housing, wherein an air inlet hole and an air outlet hole are disposed on the housing;
 a beauty component, disposed in the housing; and
 a heat dissipation component, disposed in the housing, and comprising an airflow generation apparatus and a heat sink, the airflow generation includes a fan, the fan generates cooling air to be blown to the heat sink, so as to dissipate heat for the heat sink, the heat sink is configured to absorb heat in the housing, the outer surface of the heat sink has a plurality of side walls;

wherein the heat sink has a first air outlet communicating with the air outlet hole, an air inlet communicating with an air outlet of the airflow generation apparatus, and a second air outlet that is located on a different side wall of the heat sink from the first air outlet, and a size of the second air outlet is less than a size of the first air outlet;

wherein the second air outlet allows a cooling airflow generated by the airflow generation apparatus to flow to a plurality of locations of the heat sink through the air inlet; during heat dissipation, the cooling airflow generated by the airflow generation apparatus flows to the inside of the heat sink through the air inlet; a part of the cooling airflow flows to the outside of the heat sink through the second air outlet, and then flows to the outside of the housing; and another part of the cooling airflow flows to the outside of the housing through the first air outlet after heat exchange is completed for the cooling airflow inside the heat sink; because the second air outlet is disposed, a difference between an internal air pressure and an external air pressure of the heat sink is reduced, heat on the heat sink can be evenly dissipated, thereby effectively alleviating a case in which the beauty instrument is locally overheated or scalded.

2. The beauty instrument according to claim 1, wherein a first gas flow channel and a cavity are disposed in the housing, and a first opening is disposed on one side wall of the first gas flow channel;

the beauty component is located in the first gas flow channel, and comprises a lamp tube and a reflector disposed around the lamp tube, the reflector is open on two opposite sides in a gas flow direction of the first gas flow channel to allow gas to pass through, and a second opening is disposed on the reflector or on one side of the reflector;

the cavity communicates, by using the first opening and the second opening, with space enclosed by the reflector, the cavity is formed with a third opening, and the third opening communicates with the air outlet hole; and an air inlet of the airflow generation apparatus communicates with the air inlet hole, the air outlet of the airflow generation apparatus communicates with a gas inlet at one end of the first gas flow channel, and a gas outlet at the other end of the first gas flow channel communicates with the air outlet hole.

3. The beauty instrument according to claim 2, wherein the beauty component further comprises a filter configured to filter light emitted by the lamp tube, the filter is opposite to the reflector, and a reflector body edge that is of the reflector and that faces the filter is notched to form the second opening, or an interval between the filter and a reflector body edge that is of the reflector and that faces the filter forms the second opening.

4. The beauty instrument according to claim 2, further comprising:

a middle frame, wherein the middle frame is located in the housing, the first gas flow channel is formed on the middle frame, the gas inlet and the gas outlet of the first gas flow channel are respectively located at two opposite ends of the middle frame, and the airflow generation apparatus is opposite to the middle frame and is connected to one end that is of the middle frame and that has the gas inlet, wherein the middle frame and the airflow generation apparatus are disposed around a circumference of the heat sink, and the two opposite ends of the middle frame are correspondingly located on two opposite sides of the heat sink.

5. The beauty instrument according to claim 4, wherein the gas outlet faces the heat sink, the gas outlet and the air outlet hole are respectively located in different side directions of the heat sink, one end that is of the middle frame and that is provided with the gas outlet is spaced apart from the heat sink to form a gas passing channel, and the gas passing channel allows gas flowing out of the gas outlet to pass through and flow to the air outlet hole.

6. The beauty instrument according to claim 4, wherein a part that is of the middle frame and that is located between the gas outlet and the gas inlet is spaced apart from the heat sink to form a gas traveling channel, the heat sink further has a second air outlet facing the middle frame, and the second air outlet communicates with the air outlet hole by using the gas traveling channel.

7. The beauty instrument according to claim 1, wherein a first gas flow channel is disposed in the housing, an air guiding structure is disposed in the first gas flow channel, and the air guiding structure guides a flow direction of gas in the first gas flow channel, so that the gas flows out through a plurality of locations of a gas outlet of the first gas flow channel to the air outlet hole of the housing.

8. The beauty instrument according to claim 7, wherein the air guiding structure is disposed on one inner wall of the first gas flow channel and extends toward the other opposite inner wall of the first gas flow channel; and in the flow direction of gas in the first gas flow channel, a distance between the air guiding structure and the other opposite inner wall of the first gas flow channel gradually decreases, to step-by-step block the gas in the first gas flow channel, so as to guide the gas to the plurality of locations of the gas outlet.

9. The beauty instrument according to claim 7, wherein the air guiding structure comprises an air guiding part, the air guiding part is step-shaped to form a plurality of first air guiding surfaces and a second air guiding surface, the plurality of first air guiding surfaces correspondingly block gas that flows at different locations in the first gas flow channel, any two adjacent first air guiding surfaces are connected by using the second air guiding surface, and the second air guiding surface guides a flow direction of gas that flows back due to blocking by the first air guiding surface, so that the gas flows to the gas outlet.

10. The beauty instrument according to claim 1, wherein the heat sink further has a third air outlet, a size of the third air outlet is less than the size of the first air outlet, and the first air outlet, the second air outlet, and the third air outlet are respectively located on different side walls of the heat sink.

11. The beauty instrument according to claim 10, wherein
the air inlet and the second air outlet are respectively located on two sides of the first air outlet, the third air outlet and the air inlet are located on a same side of the heat sink, and the third air outlet is staggered from the air inlet and away from the first air outlet.

12. The beauty instrument according to claim 11, wherein the heat sink comprises several heat dissipation fins disposed at intervals, and several openings facing different directions are formed between two adjacent heat dissipation fins; and a first stopper is disposed at each opening facing the beauty component, and the first stopper is configured to guide a cooling airflow entering from the air inlet to flow toward the first air outlet, so that the cooling airflow after heat exchange is discharged from the air outlet hole of the housing to the outside.

13. The beauty instrument according to claim 12, wherein one side edge of each heat dissipation fin extends to form a protrusion part, each protrusion part comprises a first edge and a second edge that intersect with each other, an opening between every two adjacent first edges forms the air inlet connected to the airflow generation apparatus, and a second stopper is disposed at an opening between every two adjacent second edges.

14. The beauty instrument according to claim 13, wherein each heat dissipation fin further has a third edge that is on a same side as the protrusion part and that intersects with the second edge, and an opening between every two adjacent third edges forms the third air outlet of the heat sink.

15. The beauty instrument according to claim 10, wherein the air inlet and the second air outlet are respectively located on two sides of the first air outlet, and the airflow generation apparatus and the heat sink form an included angle.

16. The beauty instrument according to claim 1, wherein the beauty component comprises:
    a light source;
    a cold compress component, disposed on a side of the light source in a light exit direction;
    a first optical element, disposed between the light source and the cold compress component;
    a second optical element, disposed between the first optical element and the cold compress component; and
    a first sealing member, disposed between the first optical element and the second optical element, and configured to seal a gap between the first optical element and the second optical element, wherein
    light emitted by the light source is exported through the first optical element, the second optical element, and the cold compress component, and the cold compress component is configured to be in contact with and care for the human skin.

17. The beauty instrument according to claim 16, wherein one of the first optical element and the second optical element is a filter, and the other thereof is a heat insulation piece; and
    the second optical element is attached to the cold compress component, or the second optical element is spaced apart from the cold compress component, and a second sealing member is disposed between the second optical element and the cold compress component.

18. The beauty instrument according to claim 1, wherein one end of the housing is provided with a first light outlet, the beauty component comprises a cold compress component, and the cold compress component is disposed in the first light outlet or the cold compress component is disposed on an outer periphery of the first light outlet; and
    the beauty instrument further comprises a beauty instrument accessory head, and the beauty instrument accessory head comprises:
    an outer cover, configured to be detachably connected to the housing, and comprising a contact outer surface and a connection outer surface;
    a conductive member, disposed on the outer cover, and comprising a first end face exposed to the contact outer surface and a second end face exposed to the connection outer surface, wherein the first end face is configured to be in contact with the human skin, and the second end face is configured to be in contact with the cold compress component when the outer cover is connected to the housing; and
    an elastic member, disposed between the outer cover and the conductive member, wherein one end of the elastic member acts on the outer cover, and the other end thereof acts on the conductive member toward the second end face, so that the conductive member is attached to the cold compress component when the outer cover is connected to the housing, wherein
    the outer cover is formed with a second light outlet, the conductive member is disposed in the second light outlet or the conductive member is disposed on an outer periphery of the second light outlet, and a size of the second light outlet is different from a size of the first light outlet.

19. The beauty instrument according to claim 18, wherein an end that is of a side wall of a beauty instrument body and that is close to the beauty instrument accessory head forms a first curved surface, the outer cover extends in directions of two sides of the second light outlet to form two connection arms, the two connection arms each are formed with a limiting slot for insertion of the side wall that is of the beauty instrument body and that has the first curved surface, and at least one inner surface of the limiting slot is a second curved surface adapted to the first curved surface.

20. The beauty instrument according to claim 19, wherein a first electrically conductive contact is disposed on the beauty instrument accessory head, a second electrically conductive contact is disposed on the beauty instrument body, and when the beauty instrument accessory head is sleeved on the housing, the first electrically conductive contact is in contact with and electrically connected to the second electrically conductive contact; and
    the outer cover is further formed with a connection bottom plate, the connection bottom plate is connected between the two connection arms, the first electrically conductive contact is disposed on the connection bottom plate, and the second electrically conductive contact is disposed on a surface that is of the beauty instrument body and that faces the connection bottom plate.

* * * * *